United States Patent [19]

Christensen et al.

[11] 4,309,438
[45] Jan. 5, 1982

[54] N-ALKYL-N-IMINOMETHYL DERIVATIVES OF THIENAMYCIN

[75] Inventors: Burton G. Christensen, Metuchen; William J. Leanza, Berkeley Heights; Kenneth J. Wildonger, Somerville, all of N.J.

[73] Assignee: Merck & Co., Inc., Rahway, N.J.

[21] Appl. No.: 135,574

[22] Filed: Mar. 31, 1980

Related U.S. Application Data

[63] Continuation of Ser. No. 962,346, Nov. 20, 1978, abandoned, which is a continuation of Ser. No. 793,975, May 5, 1977, abandoned.

[51] Int. Cl.$^3$ .................. C07D 487/04; A61K 31/40; A61K 31/44; A61K 31/425
[52] U.S. Cl. ........................ 424/274; 260/245.2 T; 424/263; 424/270; 546/272; 548/181
[58] Field of Search ............... 260/245.2 T; 424/263, 424/270, 274; 546/272; 548/181

[56] References Cited

U.S. PATENT DOCUMENTS 4,172,144  10/1979  Bouffard et al. ............ 260/245.2 T

*Primary Examiner*—Mark L. Berch

*Attorney, Agent, or Firm*—Frank M. Mahon; James A. Arno; Hesna J. Pfeiffer

[57] ABSTRACT

Disclosed are N-alkyl-N-iminomethyl derivatives of thienamycin which may be represented by the following structural formula:

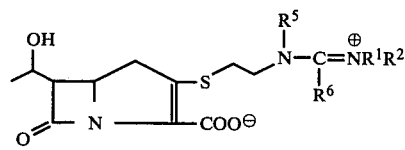

wherein $R^5$ is, inter alia, alkyl, alkenyl, aryl, or aralkyl, $R^6$ is selected from R, OR, SR and $NR^1R^2$ wherein R is, inter alia, hydrogen and substituted or unsubstituted: alkyl, alkenyl, alkynyl, cycloalkyl, cycloalkylalkyl, aryl, aralkyl, heteroaryl, heteroaralkyl, heterocyclyl, and heterocyclylalkyl; and $R^1$ and $R^2$ are hydrogen or R. Such compounds, including their O— and carboxyl derivatives are useful as antibiotics. Also dislosed are processes for the preparation of such compounds: pharmaceutical compositions comprising such compounds; and methods of treatment comprising administering such compounds and compositions when an antibiotic effect is indicated.

17 Claims, No Drawings

N-ALKYL-N-IMINOMETHYL DERIVATIVES OF THIENAMYCIN

This is a continuation, of application Ser. No. 962,346, filed Nov. 20, 1978, now ARN; which in turn is a continuation of U.S. Ser. No. 793,975 filed May 5, 1977, now abandoned.

BACKGROUND OF THE INVENTION

This invention relates to novel N-alkyl-N-iminomethyl derivatives (I) of the antibiotic thienamycin (structure II, below). Such compounds, including their O- and carboxyl derivatives and their pharmaceutically acceptable salts are useful as antibiotics. This invention also relates to processes for the preparation of such compounds, pharmaceutical compositions comprising such compounds, and methods of treatment comprising administering such compounds and compositions when an antibiotic effect is indicated. The compounds of the present invention may generically be represented by the following structural formula (I):

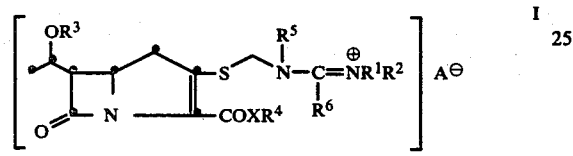

which is one canonical form of a single resonant structure:

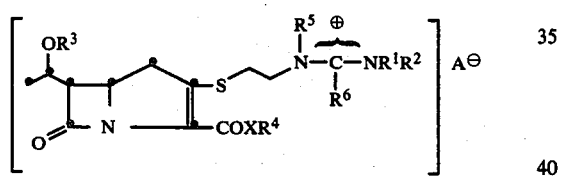

Structure I may more conveniently be represented by the symbol:

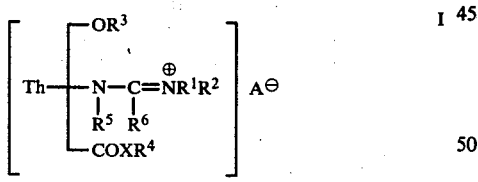

wherein: "Th" symbolizes the bicyclic nucleus of thienamycin and the OH, amino, and carboxyl groups of thienamycin are illustrated;

X is oxygen, sulphur or $NR'$ ($R'=H$ or alkyl having 1-6 carbon atoms); and $R^4$ is, inter alia, representatively selected from the group consisting of hydrogen, conventional blocking groups such as trialkylsilyl, acyl and radicals ($R^4$) giving rise to the pharmaceutically acceptable salt, ester and amide moieties (—COXR$^4$) known in the bicyclic 3-lactam antibiotic art (the definition of $R^4$ is given in greater detail below);

$R^3$ is hydrogen; or $R^3$ is (1) acyl (generically the group $OR^3$ is classifiable as an ester); or (2) $R^3$ is selected from alkyl, aryl, aralkyl and the like such that the group $OR^3$ is generically classifiable as an ether; the term "acyl" is by definition inclusive of the alkanoyls including derivatives and analogues thereof such as thio analogues wherein the carbonyl oxygen is replaced by sulphur; as well as sulphur and phosphorous acyl analogues such as substituted sulfonyl-, sulfinyl-, and sulfenyl- radicals, and substituted P(III and V) radicals such as substituted phosphorous-, phosphoric-, phosphenous- and phosphonic- radicals, respectively; such acyl radicals of the present invention are further defined below, as are the radicals 2. (above) which constitute the ether embodiments of the present invention ($R^3$ is defined in greater detail below;

$R^5$ is, inter alia, alkyl, alkenyl, aryl or aralkyl; for example, $R^5$ may be selected from the group consisting of: substituted and unsubstituted: lower alkyl having 1-10 carbon atoms, alkenyl having 2-10 carbon atoms, alkynyl having 2-10 carbon atoms, ring substituted and unsubstituted: cycloalkyl, cycloalkenyl, cycloalkenylalkyl, and cyclo-, alkylalkyl having 3-6 ring carbon atoms and 1-6 carbon atoms in the alkyl chain; aryl having 6-10 carbon atoms; aralkyl having 6-10 ring carbon atoms, and 1-6 carbon atoms in the alkyl chain; mono- and bicyclic heteroaryl and heteroaralkyl comprising 4-10 ring atoms one or more of which is selected from oxygen, nitrogen and sulphur and 1-6 carbon atoms in the alkyl chain; and wherein the ring or chain substituent (or substituents) in the aforementioned radicals is selected from: halo such as chloro, bromo, iodo and fluoro, azido, cyano, amino, mono-, di- and trialkyl substituted amino wherein the alkyl has 1-6 carbon atoms, hydroxyl, alkoxyl having 1-6 carbon atoms, alkylthioalkyl having 1-6 carbon atoms, carboxyl, oxo, alkoxylcarbonyl having 1-6 carbon atoms in the alkoxyl moiety, acyloxy comprising 2-10 carbon atoms, carbamoyl, and mono- and dialkylcarbamoyl wherein the alkyl groups have 1-4 carbon atoms, cyanothio (-SCN), and nitro; $R^5$ is further defined below:

$R^6$ is selected from the group consisting of hydrogen, R, OR SR and -NR$^1$R$^2$;

$R^1$ and $R^2$ are independently selected from R, hydrogen, nitro, hydroxyl, alkoxyl having 1-6 carbon atoms, amino, mono- di- and trialkylamino wherein the alkyl moieties each comprise 1-6 carbon atoms; $R^1$ and $R^2$ may be joined together to form a substituted or unsubstituted mono- or bicyclic heteroaryl or heterocyclyl comprising (together with the nitrogen atom to which they are attached) 4-10 atoms one or more of which may be an additional hetero atom selected from oxygen, sulphur or nitrogen; R, $R^1$ and $R^2$ are substituted or unsubstituted: cyano; carbamoyl; carboxyl; alkoxycarbonyl and alkyl having from 1 to about 10 carbon atoms; alkenyl having from 2 to about 10 carbon atoms; alkynyl having from 2 to about 10 carbon atoms; cycloalkyl having from 3 to 10 carbon atoms; cycloalkylalkyl and cycloalkylalkenyl having from 4 to 12 carbon atoms; cycloalkenyl, cycloalkenylalkenyl, and cycloalkenylalkyl having 3-10, 4-12 and 4-12 carbon atoms, respectively; aryl having from 6 to 10 carbon atoms, aralkyl, aralkenyl, and aralkynyl having from 7 to 16 carbon atoms; mono- and bicyclic heteroaryl and heteroaralkyl which typically comprise 4 to 10 ring atoms one or more of which is a hetero atom selected from oxygen, sulphur, or nitrogen and wherein the alkyl moiety of the heteroaralkyl radical comprises 1 to about 6 carbon atoms; mono- and bicyclic neterocyclyl and neterocyclylalkyl which typically comprises 4 to 10 ring atoms one or more of which is a hetero atom selected from oxygen, sulphur or nitrogen and wherein the alkyl moiety of the heterocyclylalkyl radical comprises from 1 to about 6 carbon atoms; and wherein the above-mentioned substituent or substituents on R, $R^1$, $R^2$ or on the ring formed by the joinder of $R^1$ and $R^2$, are selected from the group consisting of: halo, such as chloro, bromo, iodo and fluoro; azido; alkyl having 1–4 carbon atoms; thio; sulpho; phosphono; cyanothio (-SCN); nitro; cyano; amino; hydrazino; mono-, di- and trialkyl substituted amino, and hydrazino wherein the alkyl has 1–6 carbon atoms; hydroxyl; alkyl having 1–4 carbon atoms; alkoxyl having 1–6 carbon atoms; alkylthio having 1–6 carbon atoms; carboxyl; oxo; alkoxylcarbonyl having 1–6 carbon atoms in the alkoxyl moiety; acyloxy comprising 2–10 carbon atoms; carbamoyl and mono- and dialkylcarbamoyl wherein the alkyl groups have 1–4 carbon atoms; and the non-critical counter anion, A, is representatively selected to provide pharmaceutically acceptable salts such as halides (chloro, bromo and the like), sulfate, phosphate, citrate acetate, benzoate and the like. Relative to the definition of A, it should be noted that embodiments of the present invention wherein X=oxygen and $R^4$ is hydrogen are best considered to be zwitterions of the following structural representation (I):

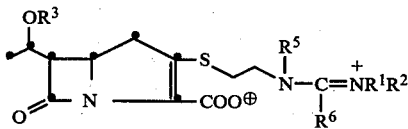

Thienamycin, the parent compounds is disclosed and claimed in U.S. Pat. No. 3,950,357 issued Apr. 13, 1976. This patent is incorporated herein by reference since thienamycin may be employed as a starting material in the preparation of the compounds of the present invention. Thienamycin is known to have the following structure:

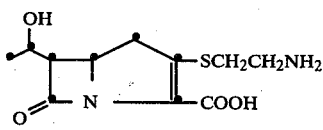

Starting material II (including all isomers and mixtures of isomers thereof) is also available by the total synthesis which is described and claimed in co-pending, commonly assigned U.S. patent application Ser. No. 792,071, filed Apr. 28, 1977, of Christensen, Johnston, Schmitt now abandoned in favor of U.S. patent application Ser. No. 17,680, filed Mar. 5, 1979, now U.S. Pat. No. 4,234,596, issued Nov. 18, 1980. This application is incorporated herein by reference since it makes available all isomers, pure and as mixture, of II which are suitable starting materials for the preparation of the compounds of the present invention. Another convenient starting material for preparation of the compounds of the present invention is N-alkylated thienamycin and its O- and carboxyl derivatives (III):

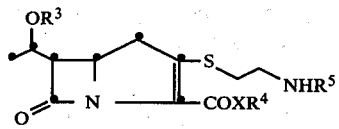

wherein $R^3$, X, $R^4$ and $R^5$ are as defined above. The N-alkylated thienamycins (III) are disclosed and claimed in co-pending U.S. patent application Ser. No. 733,611 filed Oct. 18, 1976 now abandoned in favor of U.S. patent application Ser. No. 861,235, filed Dec. 16, 1977, now U.S. Pat. No. 4,235,920, issued Nov. 25, 1980. This application is incorporated herein by reference for its disclosure relative to the preparation of N-alkyl thienamycins defined by III, above.

Reference is made to commonly assigned, co-pending U.S. patent application Ser. No. 733,654 filed Oct. 18, 1976 now abandoned in favor of U.S. patent application Ser. No. 852,425, filed Nov. 17, 1977, now U.S. Pat. No. 4,194,047, issued Mar. 18, 1980 which discloses and claims N-iminomethyl derivatives of thienamycin (IV):

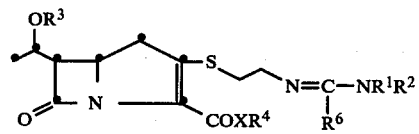

wherein $R^3$, X, $R^4$, $R^1$ and $R^2$ are as defined above. This application is incorporated herein by reference as it discloses the preparation of IV (above) from thienamycin II (above). It should be noted that the preparation of species IV from II ((II→IV) is exactly analogous to the preparation of the compounds of the present invention I from III (III→I).

Finally, reference is made to commonly assigned, concurrently filed U.S. patent application Ser. No. 793,974, (filed May 5, 1977, now U.S. Pat. No. 4,235,917, issued Nov. 25, 1980) which discloses N-alkyl, N-acyl derivatives of thienamycin:

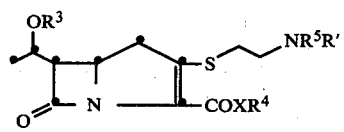

wherein $R^3$, X, $R^4$ and $R^5$ are as defined above and R' is acyl. This application is incorporated herein by reference, since the species IVa is required in the preparation of embodiments of I when $R^6$ is OR or SR.

There is a continuing need for new antibiotics. For unfortunately there is no static effectiveness of a given antibiotic because continued wide scale usage of any such antibiotic selectively gives rise to resistant strains of pathogens. In addition, the known antibiotics suffer from the disadvantage of being effective only against certain types of microorganisms. Accordingly the search for new antibiotics continues.

Unexpectedly, it has been found that the compounds of the present invention are broad spectrum antibiotics, which are useful in animal and human therapy and in inanimate systems.

Thus, it is an object of the present invention to provide a novel class of antibiotics which possess the basic nuclear structure of the antibiotic thienamycin but which are characterized as N-alkyl-N-iminomethyl derivatives thereof. These antibiotic are active against a broad range of pathogens which representatively include both gram positive bacteria such as *S. aureus, Strep. pyogenes* and *B. subtilis* and gram negative bacteria such as *E. coli, Proteus morganii, Serratia, Pseudomenas* and *Kiebsiella.* Further objects of this invention are to provide chemical processes for the preparation of such antibiotics and their non-toxic pharmaceutically acceptable salts; pharmaceutical compositions comprising such antibiotics; and to provide methods of treatment comprising administering such antibiotics and compositions when an antibiotic effect is indicated.

DETAILED DESCRIPTION OF THE INVENTION

With respect to the generic description of the present invention (structure I, above) the most preferred embodiments are those wherein $R^5$ is selected from lower alkyl and alkenyl having from 1 to 6 carbon atoms; such as methyl, ethyl, propyl, allyl and the like; benzyl and nuclear substituted benzyl such as p-t-butyl benzyl and the like; heteroaralkyls such as 4-pyridyl methyl, 2-furyl methyl, 2-thienyl methyl and the like; and $R^6$, $R^1$, $R^2$, $R^3$, X and $R^4$ are as defined above and further exemplified below. Especially preferred compounds of the present invention are those wherein $R^6$, $R^1$ and $R^2$ are as defined in this paragraph; X is oxygen, $R^3$ is hydrogen, and $R^4$ is hydrogen or a pharmaceutically acceptable salt.

The compounds of the present invention are most conveniently prepared by derivatizing a suitably substituted N-alkyl thienamycin:

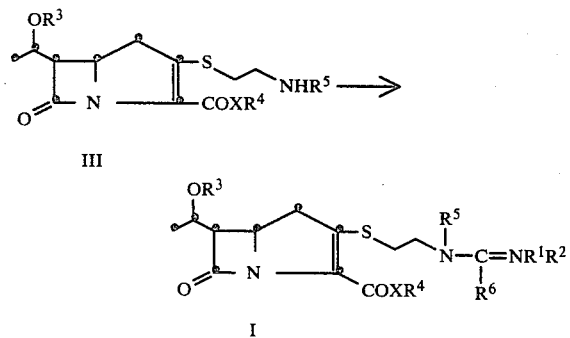

For embodiments of the present invention wherein $R^6$ is OR or S R, starting material IVa (above) is used; wherein the acyl radical R' is the carbamyl or thiocarbamyl radical of choice.

As mentioned above, the reaction (III→I or IVa→I) is perfectly analogous to the reaction (II→IV) described in co-pending, incorporated-by-reference U.S. patent application Ser. No. 733,654 filed Oct. 18, 1976: now abandoned in favor of U.S. patent application Ser. No. 852,425, filed Nov. 17, 1977, now U.S. Pat. No. 4,194,047, issued Mar. 18, 1980

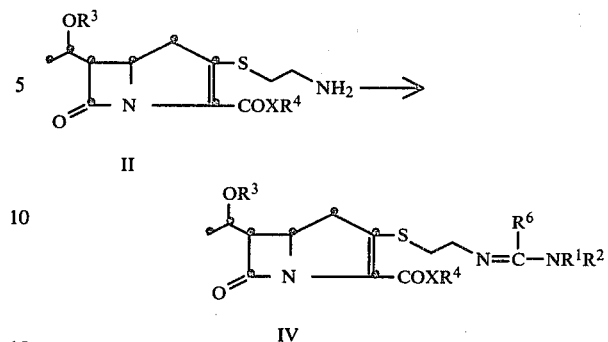

except that starting material II (or its O-; and/or carboxyl derivatives) is replaced by an equivalent amount of starting material III (or IVa).

The starting material III is fully disclosed and claimed in co-pending, commonly assigned U.S. patent application Ser. No. 733,611 filed Oct. 18, 1976, now abandoned in favor of U.S. patent application Ser. No. 861,235, filed Dec. 16, 1977, now U.S. Pat. No. 4,235,920, issued Nov. 25, 1980. This co-pending application is thus incorporated herein by reference for its disclosure relative to the preparation of N-monoalkyl thienamycin derivatives (III).

Such N-monoalkyl thienamycin derivatives are prepared by reacting thienamycin or a suitable derivative thereof or a suitably protected thienamycin species with an N-alkylating agent. There is no undue criticality in the process and any of a variety of well-known N-alkylation procedures may be employed. The identity of the N-alkylating agent is a matter of choice within the limits set by the definition of $R^1$. The N-alkylation may be conducted in any of a variety of solvent systems which are inert or substantially inert to the desired course of reaction. Suitable solvents include polar solvents such as water, lower alkanoyls such as ethanol, dioxane, tetrahydrofuran (THF), acetonitrile, hexamethylphosphoramide (HMPA), dimethylformamide (DMF) and the like and mixtures (particularly aqueous mixtures) of the above; and non-polar solvents such as benzene and halohydrocarbons such as methylene chloride, chloroform and the like. Typically the reaction is conducted at a temperature of from −40° C. to 50° C. for from a few minutes to 5 hours. Usually, the reaction is conducted in the presence of an acid acceptor such as propylene oxide, magnesium oxide, potassium carbonate and the like. The preferred N-alkylating agents include active halides, sulfate esters, and Michael addition reagents. The following reagents are representative of such alkylating agents: methyl iodide, allyl bromide, bromo acetone, phenacyl bromide, benzyl bromide, ethylchloroacetate, propargyl bromide, 2-bromoethylethylether, dimethyl sulfate, methylfluorosulphonate, chloromethylthiocyanate, chloroethylmethylsulfide, bromomethylcyclopropane, 2,4-dinitrofluorobenzene, 2-chloromethylpyridine, acrylonitrile, methyl methacrylate, nitroethylene and the like.

The starting material III, may be prepared in any of a variety of ways. One convenient starting material is tris-trimethylsilyl thienamycin [Th(TMS)₃] (see below). When it is desired for $R^3$, $R^4$ or $R^3$ and $R^4$ to be other than hydrogen, suitably derivatized starting materials such as Ia, Ib and Ic (below), may be employed.

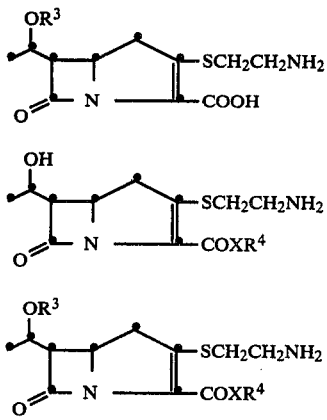

wherein $R^3$, X and $R^4$ are as defined above and further exemplified below. Starting materials Ia, Ib and Ic, which are also useful as antibiotics, are disclosure and claimed in co-pending, concurrently filed U.S. patent application Ser. Nos. 733,655, 733,651, 733,652, respectively; all filed Oct. 18, 1976, all now abandoned in favor of, respectively. U.S. patent application Ser. No. 861,234, filed Dec. 16, 1977, now U.S. Pat. No. 4,208,330, issued June 17, 1980; U.S. patent application Ser. No. 861,314, filed Dec. 16, 1977, now U.S. Pat. No. 4,181,733, issued Jan. 1, 1980; and U.S. patent application Ser. No. 861,246, filed Dec. 16, 1977, now U.S. Pat. No. 4,226,870, issued Oct. 7, 1980.

These applications are incorporated herein by reference since they describe useful starting materials for preparing III, and, additionally, analogous processes for converting the N-alkylated N-iminomethyl thienamycins of the present invention to carboxyl-, O-; and carboxyl- and O-derivatized forms which are also embraced by the present invention and are useful as antibiotics.

As stated above, the N-alkylation reaction is carried out in any of the above-named, solvents in the presence of the N-alkylating agent of choice, such as, $R^4X'$, wherein X' is a leaving group such as halo or a sulphate ester. When using, for example, the above-mentioned Th(TMS)$_3$ then the desired product is obtained by aqueous hydrolysis following the N-alkylation step. The following reaction diagram summarizes the process:

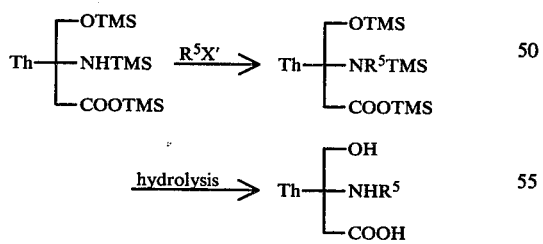

wherein TMS is trimethylsilyl, and $R^5$ and X' are as defined above.

A second scheme for the preparation of monoalkyl thienamycins (III) involves the N-alkylation of an N-substituted thienamycin wherein the substituent is an easily removable, bulky group ($R^3$) such as an aralkyl group, for example substituted and unsubstituted: benzyl, benzylhydryl (—CH(C$_6$H$_5$)$_2$) and trityl (—C(C$_6$H$_5$)$_3$) wherein the ring substituent on the aralkyl may be halo, nitro, loweralkyl, loweralkoxyl or the like. The following reaction diagram summarizes this scheme:

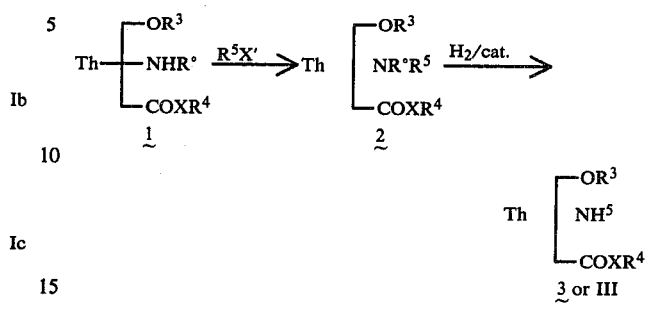

wherein all symbolism is as defined above.

In words relative to the above diagram, starting material 1, prepared for example from the reaction of thienamycin or derivative thereof with an aralkyl halide, is reacted with the N-alkylating agent of choice $R^1X'$, as above-described, to provide the N,N-dialkyl intermediate 2. The aralkyl N-substituent $R^O$ is readily removable to provide 3 by hydrogenolysis. Suitable conditions for this final cleavage step involve hydrogenating 2 in a solvent such as ethanol under hydrogen (1 to 4 atmospheres) in the presence of a catalyst such as platinum, palladium, or oxides thereof. The ultimate product of this reaction is primarily 3, the N-monoloweralkyl species. However, there is some co-presence of N,N-diloweralkyl thienamycin. Such contaminating by-products may be separated by chromatographic methods and the magnitude of contamination may be minimized by employing one equivalent or less of the alkylating agent $R^5X'$.

A third method for the preparation of N-monoalkyl species, III, particularly N-loweralkyl species, is similar to the above described procedure except that the starting material 1a is N,N-diaralkyl thienamycin. The preparation of such starting materials is described below. The following reaction diagram summarized this process:

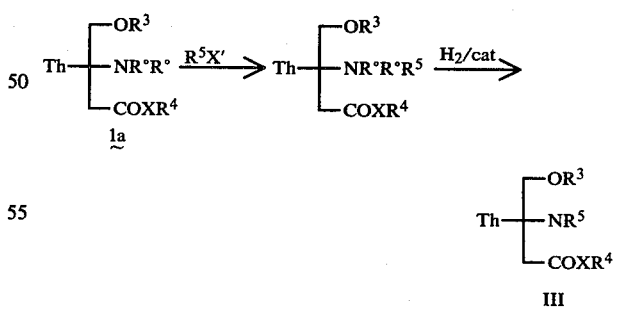

wherein all symbolism is as described above. It is to be noted that this scheme for the preparation of N-loweralkyl thienamycins is not complicated by the co-preparation of N,N-diloweralkyl thienamycins.

A fourth method which is particularly suitable for the preparation of N-loweralkyl thienamycins species (III) involves the N-alkylation of a Schiff's Base of thienamycin. The following diagram summarizes the reaction.

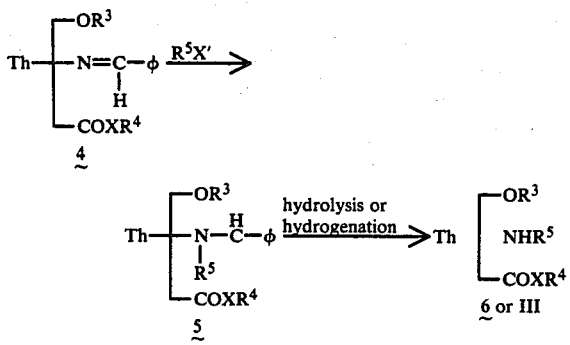

wherein all symbolism is as previously defined and in addition φ is phenyl, R⁴ and R³ may be the trimethylsilyl radical (TMS) and X may be oxygen. The preferred Schiff's base is that obtained by reacting thienamycin with benzaldehyde or nuclear substituted benzaldehyde. There is no criticality in the process for preparing such Schiff's bases and their preparation is disclosed in co-pending, commonly assigned U.S. patent application Ser. No. 733,656 filed Oct. 18, 1976, now abandoned in favor of U.S. patent application Ser. No. 907,643, filed May 19, 1978, now U.S. Pat. No. 4,172,144, issued Oct. 23, 1979. This co-pending application is incorporated herein by reference as it describes the preparation of starting material 4. The reaction of 4 with the alkylating reagent R⁵X' provides intermediate 5 which upon aqueous hydrolysis or catalytic hydrogenolysis provides the desired N-loweralkyl thienamycin species 6.

A fifth method for preparing N-loweralkyl thienamycins (III) involves the desulfurization of an N-thioacyl thienamycin in the presence of a hydrogenation catalyst such as Raney Nickel:

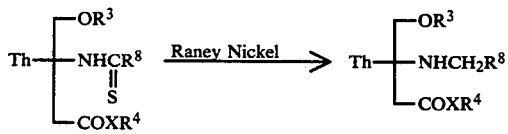

wherein X is oxygen, R³ and R⁴ are as previously defined but preferably are hydrogen, and R⁸ is hydrogen, aryl or a lower alkyl moiety having 1–5 carbon atoms. The N-thioacyl thienamycin starting materials are fully disclosed in co-pending U.S. patent application Ser. No. 733,653 filed Oct. 18, 1976, now abandoned in favor of U.S. patent application Ser. No. 160,718, filed June 18, 1980, which application is incorporated herein by reference for its disclosure relative to the preparation of such starting materials. The above desulfurization is typically conducted in polar protic solvents such as water, lower alkanols such as ethanol, and aqueous mixtures thereof at a temperature of from 0°–50° C. for from 2 minutes to 5 hours.

Identification of the Radical —COXR⁴

In the generic representation of the compounds of the present invention (I, above), the radical represented by —COXR⁴, is, inter alia, —COOH (X is oxygen and R⁴ is hydrogen) and all radicals known to be effective as pharmaceutically acceptable salt, ester, anhydride (R⁴ is acyl) and amide radicals in the bicyclic β-lactam antibiotic art, such as the cephalosporins and penicillins and the nuclear analogues thereof.

Suitable radicals (R⁴) include conventional protecting or carboxyl blocking groups. The term "blocking group" as utilized herein is employed in the same manner and in accordance with the teaching of U.S. Pat. No. 3,697,515 which is incorporated herein by reference. Pharmaceutically acceptable thienamycin derivatives of the present invention falling in this class are given below. Suitable blocking esters thus include those selected from the following list which is representative and not intended to be an exhaustive list of possible ester groups, wherein X=O and R⁴ is given:

(i) R⁴=CRᵃRᵇRᶜ wherein at least one of Rᵃ, Rᵇ and Rᶜ is an electron-donor, e.g., p-methoxyphenyl, 2,4,6-trimethylphenyl, 9-anthryl, methoxy, CH₂SCH₃, tetrahydrofur-2-yl, tetrahydropyran-2-yl or fur-2-yl. The remaining Rᵃ, Rᵇ and Rᶜ groups may be hydrogen or organic substituting groups. Suitable ester groups of this type include p-methoxybenzyloxycarbonyl and 2,4,6-trimethylbenzyloxycarbonyl.

(ii) R⁴=CRᵃRᵇRᶜ wherein at least one of Rᵃ, Rᵇ and Rᶜ is an electron-attracting group, e.g., benzoyl, p-nitrophenyl, 4-pyridyl, trichloromethyl, tribromomethyl, iodomethyl, cyanomethyl, ethoxycarbonylmethyl, arylsulphonylmethyl, 2-dimethylsulphoniummethyl, o-nitrophenyl or cyano. Suitable esters of this type include benzoylmethoxycarbonyl, p-nitrobenzyloxycarbonyl, 4-pyridylmethoxycarbonyl, 2,2,2-trichloroethoxycarbonyl and 2,2,2-tribromoethoxycarbonyl.

(iii) R⁴=CRᵃRᵇRᶜ wherein at least two of Rᵃ, Rᵇ and Rᶜ are hydrocarbon such as alkyl, e.g., methyl or ethyl, or aryl, e.g., phenyl and the remaining Rᵃ, Rᵇ and Rᶜ group, if there is one, is hydrogen. Suitable esters of this type include t-butyloxycarbonyl, t-amyloxycarbonyl, diphenylmethoxycarbonyl and triphenylmethoxycarbonyl.

(iv) R⁴=Rᵈ, wherein Rᵈ is adamantyl, 2-benzyloxyphenyl, 4-methylthiophenyl or tetrahydropyran-2-yl.

Silyl esters, under this category or blocking groups, may conveniently be prepared from a halosilane or a silazane of the formula:
R⁴'₃SiX'; R⁴'₂SiX'₂; R⁴'₃Si.NR⁴'₂; R⁴'₃Si.NH.COR⁴'; R⁴'₃Si.NH.CO.NH.SiR⁴'₃; R⁴'NH.CO.NH.SiR⁴'₃; or R⁴'C(OSiR⁴'₃);

HN(SiR⁴'₃)₂ wherein X' is a halogen such as chloro or bromo and the various groups R⁴', which can be the same or different, represent hydrogen atoms or alkyl, e.g., methyl, ethyl, n-propyl, iso-propyl; aryl, e.g., phenyl; or aralkyl, e.g., benzyl groups.

More generally stated, pharmaceutically acceptable carboxyl derivatives of the present invention are those derived by reacting thienamycin or an N-protected thienamycin such as III or an N-acylated thienamycin or a species of the present invention I with alcohols, phenols, mercaptans, thiophenols, acylating reagents and the like which then may be derivatized to establish the R³ group of the compounds of the present invention (I, above). For example, esters and amides of interest are the compounds of formula I (above) having the following group at the 2-position: —COXR⁴ wherein X is oxygen, sulfur, or NR' (R' is H or R⁴), and R⁴ is alkyl having 1–10 carbon atoms, straight or branched, such as methyl, ethyl, t-butyl, pentyl, decyl and the like, carbonylmethyl, including phenacyl, p-bromophenacyl, t-t-butylphenacyl, acetoxyacetylmethyl, pivaloxyacetylmethyl, carboxymethyl, and its alkyl and aryl esters, α-carboxy-α-isopropyl; aminoalkyl including 2-methylaminoethyl, 2-diethylaminoethyl, 2-acetamidoethyl, phthalimidomethyl, succinimidomethyl, alkoxyalkyl wherein the alkoxy portion has 1-10 and preferably 1-6 carbon atoms; but can be branched, straight or cyclic, and the alkyl portion has 1-6 carbon atoms, such as methoxymethyl, ethoxymethyl, isopropoxymethyl, decyloxymethyl, ethoxypropyl, decyloxypentyl, cyclohexyloxymethyl and the like; alkanoyloxyalkyl wherein the alkanoyloxy portion is straight or branched and has 1-6 carbon atoms and the alkyl portion has 1-6 carbon atoms, such as acetoxymethyl, pivaloyloxymethyl, acetoxyethyl, propionyloxyethyl, acetoxypropyl, and the like; haloalkyl wherein halo is chloro, bromo, fluoro, or iodo, and the alkyl portion is straight or branched having 1-6 carbon atoms, e.g., 2,2,2-trichloroethyl, trifluoroethyl,2-bromopropyl, diiodomethyl, 2-chloroethyl, 2-bromoethyl, and the like; alkenyl having 1-10 carbon atoms, either straight or branched, e.g., allyl, 2-propenyl, 3-butenyl, 4-butenyl, 4-pentenyl, 2-butenyl, 3-pentenyl, 3-methyl-3-butenyl, metallyl, 1,4-cyclohexadien-1-yl-methyl, and the like alkynyl having 1-10 carbon atoms, either straight or branched e.g., 3-pentenyl, propargyl, ethynyl, 3-butyn-1-yl, and the like; alkanoyl, either straight or branched, having 1-10 carbon atoms, such as pivaloyl, acetyl, propionyl, and the like; aralkyl or heteroaralkyl wherein alkyl has 1-3 carbon atoms, and hetero means 1-4 hetero atoms being selected from the group consisting of O, S, or N, such as benzyl, benzhydryl, and substituted benzyl, benzhydryl, or e.g., benzyl or benzhydryl substituted with 1-3 substituents such as benzyl, phenoxy, halo, loweralkyl, loweralkanoyloxy of 1-5 carbon atoms, lower alkoxy, hydroxy, nitro, blocked carboxy, or combinations thereof, e.g., p-chlorobenzyl, o-nitrobenzyl, 3,5-dinitrobenzyl, p-methoxybenzyl, m-benzoylbenzyl, p-t-butylbenzyl, m-phenoxybenzyl, p-benzoylbenzyl, p-nitrobenzyl, 3,5-dichloro-4-hydroxybenzyl, p-methoxycarbonylbenzyl, p-methoxybenzhydryl, p-carboxybenzyl, the latter being either the free acid, ester or the sodium salt, 2,4,6-trimethylbenzyl, p-pivaloyloxybenzyl, p-t-butoxycarbonyl benzyl, p-methylbenzyl, p-benzoyloxybenzyl, p-acetoxybenzyl, p-2-ethylhexanoylbenzoyl, p-ethoxycarbonylbenzyl, p-benzoylthiobenzyl, p-benzamidobenzyl, o-pivaloyloxybenzyl, m-pivaloyloxybenzyl, p-isopropoxybenzyl, p-t-butoxybenzyl, as well as the cyclic analogues thereof, 2,2-dimethyl-5-coumaranmethyl, 5-indanylmethyl, p-trimethylsilylbenzyl, 3,5-bis-t-butoxy-4-hydroxybenzyl; 2-thienylmethyl, 2-furylmethyl, 3-t-butyl-5-isothiazolmethyl, 6-pivaloyloxy-3-pyridazinylethyl, 5-phenylthio-1-tetrazolylmethyl, or the like (the use of the terms lower alkyl or lower alkoxy in this context means 1-4 carbon atoms chain); or phthalidyl; or phenylethyl, 2-(p-methylphenyl)ethyl, and the arylthioalkyl analogues, aryloxyalkyl wherein aryl is preferably a phenyl ring having 0-3 substituents preferably 0 or 1 substituents in the ortho or para positions and alkyl is 1-6 carbon atoms, e.g., (4-methoxy)-phenoxymethyl, phenoxymethyl, (4-chloro)phenoxymethyl, (4-nitro)phenoxymethyl, (4-benzyloxy)-phenoxymethyl, (4-methyl)phenoxymethyl, (4-benzyloxy)phenoxymethyl, (4-methyl)phenoxymethyl, (2-methoxy)phenoxymethyl, (1-phenoxy)ethyl, (4-amino)-phenoxymethyl, (4-methoxy)phenylthiomethyl, (4-chloro)phenylthiomethyl, phenylthioethyl; aryl wherein aryl is phenyl, 5-indanyl, or substituted phenyl having 0-3 substituents, preferably 0 or 1 substituent in the ortho or para position, e.g., (4-methyl)phenyl, (4-hydroxy)phenyl, (4-t-butyl)phenyl, p-nitrophenyl, 3,5-dinitrophenyl, or p-carboxyphenyl, the latter having either the free acid or the sodium salt form; aralkenyl wherein aryl is phenyl and alkenyl has 1-6 carbon atoms, such as 3-phenyl-2-propenyl; aralkoxyalkyl wherein aralkoxy is benzyloxy, and alkyl has 1-3 carbon atoms, such as benzyloxymethyl, (4-nitro)benzyloxymethyl, (4-chloro)benzyloxymethyl; alkylthioalkyl wherein the alkylthio portion has 1-10 and preferably 1-6 carbon atoms, but can be branched, straight or cyclic, and the alkyl portion has 1-6 carbon atoms, such as methylthioethyl, ethylthioethyl, cyclohexylthiomethyl, decylthiobutyl, methylthiopropyl, isopropylthioethyl, methylthiobutyl and the like.

In addition to the esters (and thio esters) listed above, amides are also embraced by the present invention, i.e., wherein X is the

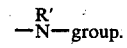
group.

Representative of such amides are those wherein R' is selected from the group consisting of hydrogen, methyl, ethyl, phenyl, p-methoxyphenyl, benzyl, carboxymethyl, methylthioethyl, and heteroaryl; also embraced by —COXR$^4$ are anhydrides wherein R$^4$ is benzyloxycarbonyl, ethoxycarbonyl, benzoyl, and pivaloyl.

The most preferred —COXR$^4$ radicals of the present invention are those wherein (relative to Structure I above) X is oxygen, sulphur or NR' (R' is selected from the group consisting of hydrogen and lower alkyl); and R$^4$ is selected from the group consisting of: loweralkyl, lower alkenyl, such as methallyl, 3-methyl butenyl, 3-butenyl, and the like; methylthioethyl; benzyl and substituted benzyl such as p-t-butylbenzyl, m-phenoxybenzyl, p-pivaloyloxybenzyl, p-nitrobenzyl and the like; pivaloyloxymethyl, 3-phthalidyl and acetoxymethyl, propionyloxymethyl, acetylthiomethyl, pivaloylthiomethyl, allyl, 4-butenyl, 2-butenyl, 3-methyl-2-butenyl, phenacyl, acetoxyacetylmethyl, methoxymethyl, p-acetoxybenzyl, p-pivaloyloxybenzyl, p-isopropoxybenzyl, 5-indanylmethyl, 5-indanyl, benzyloxymethyl, ethylthioethyl, methylthiopropyl, methoxycarbonyloxymethyl, ethoxycarbonyloxymethyl, dimethylaminoacetoxymethyl, crotonolacton-3-yl, and acetamidomethyl.

Identification of R$^3$

In the generic representation of the present invention, structure I (above), the radical R$^3$ is, in addition to hydrogen, 1.) acyl (generically the group —OR$^3$ is classifiable as an ester); or 2.) R$^3$ is selected from alkyl, aryl, aralkyl, and the like such that the group —OR$^3$ is classifiable as an ether. For the ester embodiments (1) R$^3$ is selected from the following definition of acyl radicals (p=1). In the so-called ether embodiments (2.) of the present invention, R$^3$ is selected from the same acyl radicals wherein the carbonyl moiety,

or more generally

is deleted (p=0); thus $R^3$ is selected from the following radicals wherein all symbolism is defined below.

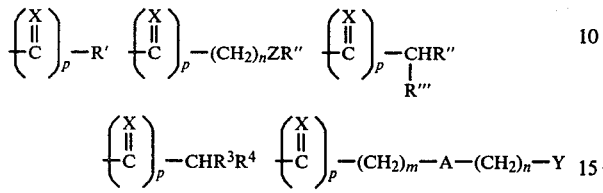

Thus, relative to the definition of $R^3$ and $R^2$, the acyl radical can, inter alia, be substituted or unsubstituted aliphatic, aromatic or heterocyclic, araliphatic or heterocyclylaliphatic carboxylic acid radical, a substituted or unsubstituted carbamyl radical or a carbothioic acid radical. One group of acyl radicals can be represented by the general formula:

wherein X is O or S and R" represents hydrogen; amino; substituted amino such as alkyl- and dialkyl-amino wherein the alkyl radical comprises 1 to about 6 carbon atoms; substituted or unsubstituted: straight or branched chain alkyl wherein the alkyl radical comprises 1 to about 6 carbon atoms; mercapto aryloxy, typically comprising 6 to 10 carbon atoms; alkenyl, or alkynyl groups typically comprising 2 to 6 carbon atoms; aryl such as phenyl; aralkyl such as benzyl; cycloalkyl, typically comprising 3 to 6 carbon atoms; or a heteroaryl or heteroaralkyl group (mono- and bicyclic) wherein the alkyl moiety typically comprises 1 to 3 carbon atoms and the heterocyclic ring comprises typically 4 to 10 atoms and the hetero atom or atoms are selected from O, N and S; such above-listed groups can be unsubstituted or can be substituted by radicals such as OH, SH, SR (R is lower alkyl or aryl such as phenyl; alkyl or alkoxy groups having 1 to about 6 carbon atoms, halo, such as Cl, Br, R and I, cyano, carboxy, sulfamino, carbamoyl, sulfonyl, azido, amino, substituted amine such as alkylamine including quaternary ammonium wherein the alkyl group comprises 1 to 6 carbon atoms, haloalkyl such as trifluoromethyl, carboxyalkyl, carbamoylalkyl, N-substituted carbamoylalkyl, wherein the alkyl moiety of the foregoing four radicals comprises 1 to about 6 carbon atoms, amidino, guanidino, N-substituted guanidino, guanidino lower alkyl and the like. Representative examples of such acyl groups that might be mentioned are those wherein R" is benzyl, p-hydroxybenzyl, 4-amino-4-carboxybutyl, methyl, cyanomethyl, 2-pentenyl, n-amyl, n-heptyl, ethyl 3- or 4-nitrobenzyl, phenethyl, β,β-diphenylethyl, methyldiphenylmethyl, triphenylmethyl, 2-methoxyphenyl, 2,6-dimethoxyphenyl, 2,4,6-trimethoxyphenyl, 3,5-dimethyl-4-isoxazolyl, 3-butyl-5-methyl-4-isoxazolyl, 5-methyl-3-phenyl-4-isoxazolyl, 3-(2-chlorophenyl)-5-methyl-4-isoxazolyl, 3-(2,6-dichlorophenyl)5-methyl-4-isoxazolyl, D-4-amino-4-carboxybutyl, D-4N-benzoylamino-4-carboxy-n-butyl, p-aminobenzyl, o-aminobenzyl, m-aminobenzyl, p-dimethylaminobenzyl, (3-pyridyl)methyl, 2-ethoxy-1-napthyl, 3-carboxy-2-quinoxalinyl, 3-(2,6-dichlorophenyl)-5-(2-furyl)-4-isoxazolyl, 3-phenyl-4-isoxazolyl, 5-methyl-3-(4-guanidinophenyl)4-isoxazolyl, 4-guanidinomethylphenyl, 4-guanidinomethylbenzyl, 4-guanidinobenzyl, 4-guanidinophenyl, 2,6-dimethoxy-4-guanidino, o-sulfobenzyl, p-carboxymethylbenzyl, p-carbamoylmethylbenzyl, m-fluorobenzyl, m-bromobenzyl, p-chlorobenzyl, p-methoxybenzyl, 1-naphthylmethyl, 3-isothiazolylmethyl, 4-isothiazolylmethyl, 5-isothiazolylmethyl, guanylthiomethyl, 4-pyridylmethyl, 5-isoxazolylmethyl, 4-methoxy-5-isoxazolylmethyl, 4-methyl-5-isoxazolylmethyl, 1-imidazolylmethyl, 2-benzofuranylmethyl, 2-indolylmethyl, 2-phenylvinyl, 2-phenylethynyl, 1-aminocyclohexyl, 2- and 3-thienylaminomethyl, 2-(5-nitrofuranyl)-vinyl, phenyl, o-methoxyphenyl, o-chlorophenyl, o-phenylphenyl, p-aminomethylbenzyl, 1-(5-cyanotriazolyl)-methyl, difluoromethyl, dichloromethyl, dibromomethyl, 1-(3-methylimidazolyl)methyl, 2- or 3-(5-carboxymethylthienyl)methyl, 2- or 3-(4-carbamoylthienyl)methyl, 2- or 3-(5-methylthienyl)methyl, 2- or 3-(methoxythienyl)methyl, 2- or 3-(4-chlorothienyl)methyl, 2- or 3-(5-sulfothienyl)-methyl, 2- or 3-(5-carboxythienyl)methyl, 3-(1,2,5-thiadiazolyl)methyl, 3-(4-methoxy-1,2,5-thiadiazolyl)methyl, 2-furylmethyl, 2-(5-nitrofuryl)-methyl, 3-furylmethyl, 2-thienylmethyl, 3-thienylmethyl, tetrazolylmethyl, benzamidinomethyl and cyclohexylamidinomethyl.

The acyl group can also be a radical of the formula:

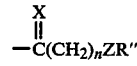

wherein X is O or S and n is 0–4, Z represents oxygen, sulfur, carbonyl or nitrogen and R" is defined as above. Representative members of the substituent

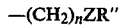

that might be mentioned are allylthiomethyl, phenylthiomethyl, butylmercaptomethyl, α-chlorocrotylmercaptomethyl, phenoxymethyl, phenoxyethyl, phenoxybutyl, phenoxybenzyl, diphenoxymethyl, dimethylmethoxyethyl, dimethylbutoxymethyl, dimethylphenoxymethyl, 4-guanidinophenoxymethyl, 4-pyridylthiomethyl, p-(carboxymethyl)phenoxymethyl, p-(carboxymethyl)phenylthiomethyl, 2-thiazolylthiomethyl, p-(sulfo)phenoxymethyl, p-(carboxymethyl)phenylthiomethyl, 2-pyrimidinyl-thiomethyl, phenethylthiomethyl, 1-(5,6,7,8-tetrahydronaphthyl)oxomethyl, N-methyl-4-pyridylthio, benzyloxy, methoxy, ethoxy, phenoxy, phenylthio, amino, methylamino, dimethylamino, pyridinium methyl, trimethylammoniummethyl, cyanomethylthiomethyl, trifluoromethylthiomethyl, 4-pyridylethyl, 4-pyridylpropyl, 4-pyridylbutyl, 3-imidazolylethyl, 3-imidazolylpropyl, 3-imidazolylbutyl, 1-pyrroloethyl, 1-pyrrolopropyl, and 1-pyrrolobutyl.

Alternatively, the acyl group can be a radical of the formula:

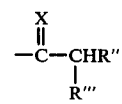

wherein R″ is defined as above and R‴ is a radical such as amino, hydroxy, azido, carbamoyl, guanidino, amidino, acyloxy, halo, such as Cl, F. Br, I, sulfamino, tetrazolyl, sulfo, carboxy, carbalkoxy, phosphono and the like. Representative members of the substituent

that might be mentioned are α-aminobenzyl, α-amino-(2-thienyl)methyl, α-(methylamino)benzyl, α-aminomethylmercaptopropyl, α-amino-3- or 4-chlorobenzyl, α-amino-3- or 4-hydroxybenzyl, α-amino-2,4-dichlorobenzyl, α-amino-3,4-dichlorobenzyl, D-(—)-α-hydroxybenzyl, α-carboxybenzyl, α-amino-(3-thienyl)methyl D(—)-α-amino-3-chloro-4-hydroxybenzyl, α-amino(cyclohexyl)methyl, α-(5-tetrazolyl)benzyl, 2-thienyl-carboxymethyl, 3-thienyl-carboxymethyl, 2-furylcarboxymethyl, 3-furyl-carboxymethyl, α-sulfaminobenzyl, 3-thienyl-sulfaminomethyl, α-(N-methylsulfamino)-benzyl D(—)-2-thienyl-guanidinomethyl, D(—)-α-guanidinobenzyl α-guanylureidobenzyl, α-hydroxybenzyl, α-azidobenzyl, α-fluorobenzyl, 4-(5-methoxy-1,3-oxadiazolyl)-aminomethyl, 4-(5-methoxy-1,3-oxadiazolyl)-hydroxymethyl, 4-(5-methoxy-1,3-sulfadiazolyl)-hydroxymethyl, 4-(5-chlorothienyl)-aminomethyl, 2-(5-chlorothienyl)-hydroxymethyl, 2-(5-chlorothienyl)-carboxy-methyl, 3-(1,2-thiazolyl)-aminomethyl, 3-(1,2-thiazolyl)-hydroxymethyl, 3-(1,2-thiazolyl)-carboxymethyl, 2-(1,4-thiazolyl)-aminomethyl, 2-(1,4-thiazolyl)-hydroxymethyl, 2-(1,4-thiazolyl)carboxymethyl, 2-benzothienylaminomethyl, 2-benzothienylhydroxymethyl, 2-benzothienylcarboxymethyl, α-sulfobenzyl, α-phosphonobenzyl, α-diethylphosphono, and α-monoethylphosphono. Further acyl radicals of interest in this class when X=oxygen are:

wherein R³′ and R⁴′ are as defined below. R³′ represents hydrogen, halo, such as chloro, fluoro, bromo, iodo, amino, guanidino, phosphono, hydroxy, tetrazolyl, carboxy, sulfo, or sulfamino and R⁴′ represents phenyl, substituted phenyl, a mono- or bicyclic heterocyclyl containing one or more oxygen, sulfur or nitrogen atoms in the ring, such as furyl, quinoxalyl, thienyl, quinolyl, quinazolyl, thiazolyl, siothiazolyl, tetrazolyl, oxadiazolyl, thiadiazolyl and and the like substituted heterocycles, phenylthio, phenyloxy lower alkyl of 1-6 carbon atoms, heterocyclic or substituted heterocyclic thio groups; or cyano. The substituents on the moieties, R³′ and R⁴′, can be halo, carboxymethyl, guanidino, guanidinomethyl, carboxamidomethyl, aminomethyl, nitro, methoxy or methyl. When R³′ is selected from the group consisting of hydrogen, hydroxy, amino or carboxy and R⁴′ is selected from the group consisting of phenyl, or a 5- or 6-membered heterocyclic ring having one or two sulfur, oxygen or nitrogen hetero atom such as tetrazolyl, thienyl, furyl and phenyl, the following acyl radicals are representative: phenylacetyl 3-bromophenylacetyl, p-aminomethylphenylacetyl, 4-carboxymethylphenylacetyl, 4-carboxyamidomethylphenylacetyl, 2-furylacetyl, 5-nitro-2-furylacetyl, 3-furylacetyl, 2-thienylacetyl, 5-chloro-2-thienylacetyl, 5-methoxy-2-thienylacetyl, α-guanidino-2-thienylacetyl, 3-thienylacetyl, 2-(4-methylthienyl)acetyl, 3-isothiazolylacetyl, 4-methoxy-3-isothiazolylacetyl, 4-isothiazolylacetyl, 3-methyl-4-isothiazolylacetyl, 5-isothiazolylacetyl, 3-chloro-5-isothiazolylacetyl, 3-methyl-1,2,5-oxadiazolylacetyl, 1,2,5-thiadiazolyl-4-acetyl, 3-methyl-1,2,5-thiadiazolylacetyl, 3-chloro-1,2,5-thiadiazolylacetyl, 3-methoxy-1,2,5-thiadiazolylacetyl, phenylthioacetyl, 4-pyridylthioacetyl, cyanoacetyl, 1-tetrazolylacetyl, α-fluorophenylacetyl, D-phenylglycyl, 4-hydroxy-D-phenylglycyl, 2-thienylglycyl, 3-thienylglycyl, phenylmalonyl, 3-chlorophenylmalonyl, 2-thienylmalonyl, 3-thienylmalonyl, α-phosphonophenylacetyl, α-amino cyclohexadienylacetyl, α-sulfaminophenylacetyl, α-hydroxyphenylacetyl, α-tetrazolylphenylacetyl and α-sulfophenylacetyl.

The acyl radical may also be selected from sulphur (1) and phosphorous (2) radicals:

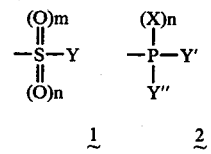

wherein with respect to 1, m and n are integers selected from 0 or 1 and Y=O⊖M⊕, —N(R″)₂, and R″; wherein M⊕ is selected from hydrogen, alkali metal cations and organic bases; and R″ is as defined above, e.g., alkyl, alkenyl, aryl and heteroaryl. With respect to 2 X=O or S; n=0 or 1; and Y′ and Y″ are selected from the group consisting of O⊖M⊕, —N(R″)₂, R″ and ZR″ wherein all symbolism is as defined above, e.g., R″ and ZR″ are representatively: alkyl, alkenyl, aryl, heteroaryloxy, Y′ and Y‴, including R″ moieties, can be joined together to form cyclic ester, ester- and amide and amide functions. Illustrative examples of the radicals 1 are methylsulphonyl, p-nitrophenylsulphonyl, p-chlorophenylsulphinyl, o-nitrophenylsulphenyl, sulfamoyl, dimethylsulphamoyl and sulpho. Illustrative examples of the radicals 2 are: dimethoxyphosphino, dibenzyloxyphosphino, dihydroxyphosphino, dimethoxyphosphinyl, dimethoxyphosphinothioyl, dibenzyloxyphosphinyl, dihydroxyphosphinyl, An acyl class of particular interest is those acyl radicals which are selected from the group consisting of conventionally known N-acyl blocking or protective groups such as carbobenzyloxy, ring-substituted carbobenzyloxy such as o- and p-nitrocarbobenzyloxy, p-methoxycarbobenzyloxy, chloroacetyl, bromoacetyl, phenylacetyl, t-butoxycarbonyl, trifluoroacetyl, bromoethoxycarbonyl, 9-fluorenylmethoxycarbonyl, dichloroacetyl, o-nitrophenylsulfenyl, 2,2,2-trichloroethoxycarbonyl, bromo-t-butoxycarbonyl, phenoxyacetyl; non-acyl protective groups such as trilower alkyl silyl, for example, trimethylsilyl and t-butyldimethyl are also of interest.

The following radicals, according to the foregoing definition of acyl, are preferred: formyl, propionyl, butyryl, chloroacetyl, methoxyacetyl, aminoacetyl, methoxycarbonyl, ethoxycarbonyl, methylcarbamoyl, ethylcarbamoyl, phenylthiocarbonyl, 3-aminopropionyl, 4-aminobutyryl, N-methylaminoacetyl, N,N-dimethylaminoacetyl, N,N,N-trimethylaminoacetyl, 3-(N,N-dimethyl)aminopropionyl, 3-(N,N,N-trimethyl)aminopropionyl, N,N,N-triethylaminoacetyl, pyridiniumacetyl, guanidinoacetyl, 3-guanidinopropionyl, N³-methylguanidinopionyl, hydroxyacetyl, 3-hydroxypropionyl, acryloyl, propynoyl, malonyl, phenoxycarbonyl, amidinoacetyl, acetamidinoacetyl, amidinopropionyl, acetamidinopropionyl, guanylureidoacetyl, guanylcarbamoyl, carboxymethylaminoacetyl, sulfoacetylaminoacetyl, phosphonoacetylaminoacetyl, $N^3$-dimethylaminoacetamidinopropionyl, ureidocarbonyl, dimethylaminoguanyl-thioacetyl, 3-(1-methyl-4-pyridinium)propionyl, 3-(5-aminoimidazol-1-yl)propionyl, 3-methyl-1-imidazoliumacetyl, 3-sydnonylacetyl, o-aminomethylbenzoyl, o-aminobenzoyl,

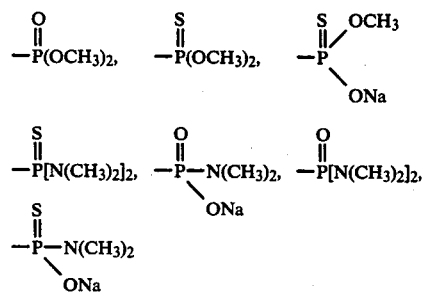

An especially preferred class of acyl radicals are terminally substituted acyls wherein the substituent is a basic group such as substituted and unsubstituted: amino, amidino, guanidino, guanyl and nitrogen-containing mono- and bicyclic heterocycles (aromatic and non-aromatic) wherein the hetero atom or atoms, in addition to nitrogen, are selected from oxygen and sulphur. Such preferred substituted acyls may be represented by the following formula:

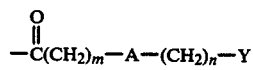

wherein m, and n are integers selected from 0 to 5; A is O, NR' (R' is hydrogen or loweralkyl having 1-6 carbon atoms), S or A represents a single bond; and Y is selected from the following group:

(1.) amino or substituted amino:

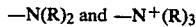

wherein the values for R are independently selected from: hydrogen; N(R')$_2$ (R' is hydrogen or loweralkyl having 1-6 carbon atoms); loweralkyl and loweralkoxyl having from 1 to 6 carbon atoms; loweralkoxyloweralkyl wherein the alkoxyl moiety comprises 1 to 6 carbon atoms and the alkyl moiety comprises 2-6 carbon atoms; cycloalkyl and cycloalkylalkyl wherein the cycloalkyl moiety comprises 3-6 carbon atoms and the alkyl moiety comprises 1-3 carbon atoms, two R groups may be joined together with the N atom to which they are attached to form a ring having 3-6 atoms.

(2.) amidino and substituted amidino:

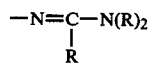

wherein the value of R is independently selected from the group consisting of: hydrogen; N(R')$_2$ (R' is hydrogen or loweralkyl having 1-6 carbon atoms); loweralkyl and loweralkoxyl having from 1 to 6 carbon atoms, loweralkoxyloweralkyl wherein the alkoxyl moiety comprises 1 to 6 carbon atoms and the alkyl moiety comprises 2 to 6 carbon atoms (when the loweralkoxyloweralkyl radical is attached to carbon the alkyl moiety comprises 1 to 6 carbon atoms); cycloalkyl and cycloalkylalkyl wherein the alkyl moiety comprises 1 to 3 carbon atoms; two R groups may be joined together with the atoms to which they are attached to form a ring having 3 to 6 atoms;

(3.) guanidino and substituted guanidino:

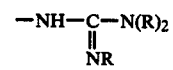

wherein R is as defined in 2. (above).

(4.) guanyl and substituted guanyl:

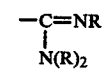

wherein R is as defined in 2. (above).

(5.) nitrogen-containing mono- and bicyclic heterocyclyls (aromatic and non-aromatic) having 4 to 10 nuclear atoms wherein the hetero atom or atoms, in addition to nitrogen, are selected from oxygen and sulphur. Such heterocyclyls are representatively illustrated by the following list of radicals (R' is H or loweralkyl having 1-6 carbon atoms):

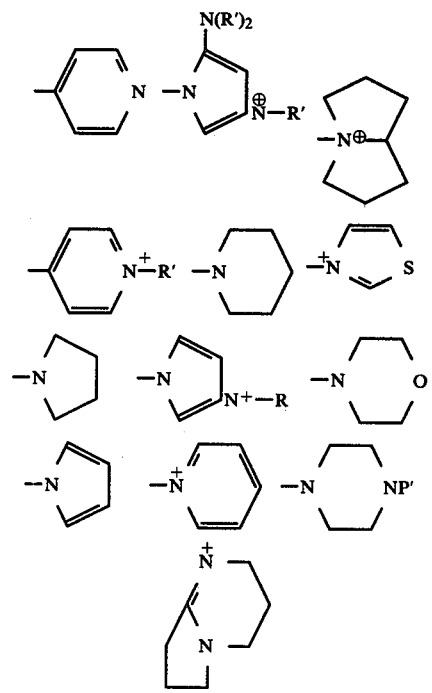

The following specific acyl radicals falling within this class are additionally representative and are preferred:

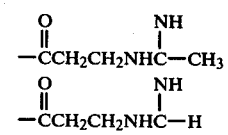

-continued

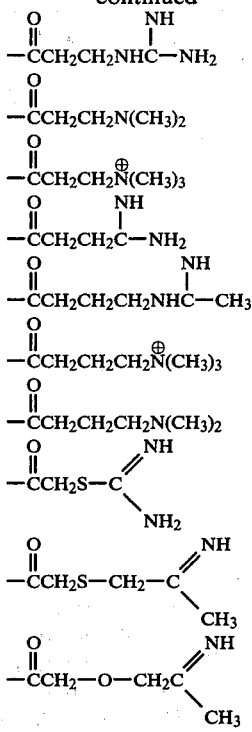

However, it is to be understood that any acyl radical may be employed in the practice of the invention and is to be considered within the scope of the invention.

Preparation of Starting Materials Ia, Ib, and Ic

The above-described starting materials are conveniently prepared from an N-protected thienamycin species such as an N-acylated thienamycin (1)

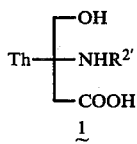

wherein $R^{2'}$ is an easily removable blocking group such as: carbobenzyloxy, ring-substituted carbobenzyloxy such as o- and p-nitrocarbobenzyloxy, p-methoxycarbobenzyloxy, chloroacetyl, bromoacetyl, phenylacetyl, t-butoxycarbonyl trifluoroacetyl, bromoethoxycarbonyl, 9-fluorenylmethoxycarbonyl, dichloroacetyl, o-nitrophenylsulfenyl, 2,2,2-trichloroethoxycarbonyl, bromo-t-butoxycarbonyl, phenoxyacetyl; non-acyl protective groups such as triloweralkylsilyl, for example, trimethylsilyl, and t-butyldimethylsilyl are also of interest. The most preferred N-blocking groups are the substituted and unsubstituted carbobenzyloxy radical:

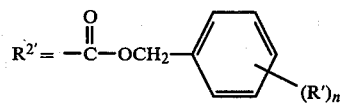

wherein n is 0–2 (n=0, R'=hydrogen) and R' is lower alkoxy or nitro; and bromo-t-butoxycarbonyl.

The ultimate N-deblocking procedure for the preparation of Ia, Ib or Ic is accomplished by any of a variety of well-known procedures which include hydrolysis or hydrogenation: when hydrogenation is employed suitable conditions involve a solvent such as a loweralkanoyl in the presence of a hydrogenation catalyst such as palladium, platinum or oxides thereof.

The N-acylated intermediate (1, above) is prepared by treating thienamycin (II) with an acylating agent, for example, an acyl halide or acyl anhydride such as an aliphatic, aromatic, heterocyclic, araliphatic or heterocyclic aliphatic carboxylic acid halide or anhydride. Other acylating agents may also be employed, for example, mixed carboxylic acid anhydrides and particularly lower alkyl esters of mixed carboxylic-carbonic anhydrides; also, carboxylic acids in the presence of a carbodiimide such as 1,3-dicyclohexylcarbodiimide, and an activated ester of a carboxylic acid such as the p-nitrophenyl ester. Such N-acylated thienamycin starting materials are fully described in the above-cited, incorporated by reference, co-pending U.S. patent application Ser. No. 733,653, filed Oct. 18, 1976, now abandoned in favor of U.S. patent application Ser. No. 160,718, filed June 18, 1980.

The acylation reaction may be conducted at a temperature in the range of from about −20° to about 100° C., but is preferably conducted at a temperature in the range of from −9° C. to 25° C. Any solvent in which the reactants are soluble and substantially inert may be employed, for example polar solvents such as water, alcohols and polar organic solvents in general such as dimethylformamide (DMF), hexamethyl phosphoramide (HMPA), acetone, dioxane tetrahydrofuran (THF), acetonitrile, heterocyclic amines such as pyridine, ethylacetate, aqueous mixtures of the above, as well as halogenated solvents such as methylene chloride and chloroform. The reaction is conducted for a period of time of from about five minutes to a maximum of three hours, but in general, a reaction time of about 0.5 to about one hour is sufficient. The following equation illustrates this process employing a carboxylic acid halide; however, it is to be understood that by substituting a carboxylic acid anhydride or other functionally equivalent acylating agent similar products may be obtained.

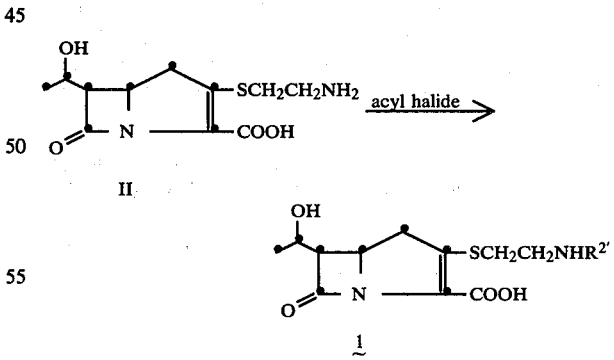

Generally when the above-described acylating reaction employs an acid halide (suitable halides are chloro, iodo, or bromo) or anhydride the reaction is conducted in water or an aqueous mixture of a polar organic solvent such as acetone, dioxane, THF, DMF, acetonitrile or the like in the presence of a suitable acceptor base such as $NaHCO_3$, MgO, NaOH, $K_2HPO_4$ and the like.

In carrying out the reactions described herein, it is generally not necessary to protect the 2-carboxy group or the 1'-hydroxy group; however, in cases where the acylating reagent is exceedingly water sensitive it is sometimes advantageous to perform the acylation in a non aqueous solvent system. Triorganosilyl (or tin) derivatives of thienamycin proceed rapidly to give the tris-triorganosilyl derivative, for example tris-trimethylsilyl thienamycin Th(TMS)$_3$:

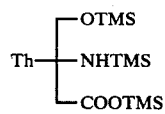

Such derivatives, which are readily soluble in organic solvents, are conveniently prepared by treating thienamycin with an excess of hexamethyldisilazane and a stoichiometric amount of trimethylchlorosilane at 25° C., with vigorous stirring under a N$_2$ atmosphere. The resulting NH$_4$Cl is removed by centrifugation and the solvent is removed by evaporation to provide the desired silyl derivative.

The intermediate starting materials Ib are prepared according to the following scheme; however, it should be noted that direct esterification, without protection of the amino group, is also possible.

wherein all symbolism is as previously defined.

In general, the transformation (1→Ib) is accomplished by conventional procedures known in the art. Such procedures include:

(1.) Reaction of 1 (or II, thienamycin) with a diazoalkane such as diazomethane, phenyldiazomethane, diphenyldiazomethane, and the like, in a solvent such as dioxane, ethylacetate, acetonitrile and the like at a temperature of from 0° C. to reflux for from a few minutes to 2 hours.

(2.) Reaction of an alkali metal salt of 1 with an activated alkyl halide such as methyliodide, benzyl bromide, or m-phenoxybenzyl bromide, p-t-butylbenzyl bromide, pivaloyloxymethyl chloride, and the like. Suitable reaction conditions include solvents such as hexamethylphosphoramide and the like at a temperature of from 0° C. to 60° C. for from a few minutes to 4 hours.

(3.) Reaction of 1 with an alcohol such as methanol, ethanol, benzyl alcohol, and the like. This reaction may be conducted in the presence of a carbodiimide condensing agent such as dicyclohexylcarbodiimide or the like. Suitable solvent, at a temperature of from 0° C. to reflux for from 15 minutes to 18 hours, include CHCl$_3$, CH$_3$CH, CH$_2$Cl$_2$ and the like.

(4.) Reaction of an N-acylated acid anhydride of 1 prepared by reacting the free acid 1 with an acid chloride such as ethylchloroformate, benzylchloroformate and the like, with an alcohol such as those listed in (3.) under the same conditions of reaction as given above for (3.). The anhydride is prepared by reacting 1 and the acid chloride in a solvent such as tetrahydrofuran (THF), CH$_2$Cl$_2$ and the like at a temperature of from 25° C., to reflux for from 15 minutes to 10 hours.

(5.) Reaction of labile esters of 1 such as the trimethylsilyl ester, dimethyl-t-butylsilyl ester or the like with R$^4$X' wherein X' is halogen such as bromo and chloro and R$^4$ is as defined, in a solvent such as THF, CH$_2$Cl$_2$ and the like at a temperature of from 0° C. to reflux for from 15 minutes to 16 hours. For example according to the following scheme:

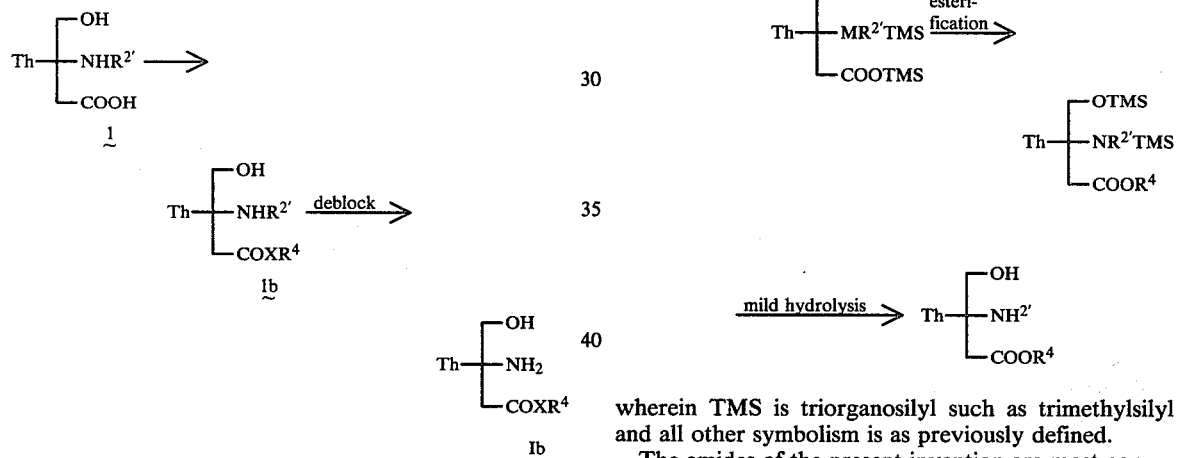

wherein TMS is triorganosilyl such as trimethylsilyl and all other symbolism is as previously defined.

The amides of the present invention are most conveniently prepared by reacting the acid anhydride of Ib (X=0, R=acyl) with ammonia or with the amine of choice, e.g., the alkyl-, dialkyl-, aralkyl- or heterocyclic amines listed above.

The above-recited schemes of esterification are well known in the related bicyclic β-lactam antibiotic art and indeed in all of general organic synthesis and it is to be noted that there is no undue criticality of reaction parameters in the preparation of the N-acylated, carboxyl derivatives Ib useful as starting materials in the practice of the present invention.

Starting materials Ia and Ic are conveniently prepared by any of a variety of well-known esterification or etherification reactions upon the secondary alcoholic group of 1b. Such procedures include:

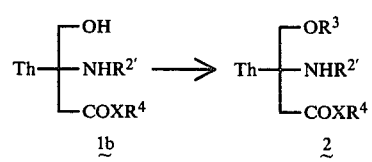

(1.) For the preparation of ether embodiments of the present invention, the acid catalized reaction of 1b with a diazoalkane such as diazomethane, phenyldiazomethane, diphenyldiazomethane and the like in an inert solvent such as dioxane, tetrahydrofuran (THF), halohydrocarbons such as $CH_2Cl_2$, ethylacetate and the like in the presence of a catalytic amount of a strong acid or Lewis acid such as toluenesulfonic acid, trifluoroacetic acid, fluoboric acid, boron trifluoride and the like at a temperature of from $-78°$ C. to $25°$ C. for from a few minutes to 2 hours.

(2) For the preparation of ether embodiments of the present invention, the reaction of 1b with an alkylating agent such as active halides, for example methyliodide, benzylbromide, m-phenoxybenzylbromide and the like; alkylsulphonates such as dimethylsulphate, diethylsulphate, methylfluorosulphonate and the like in the presence of a strong base capable of forming the alcoholate anion of Ib. Suitable bases include alkali and alkaline earth metal oxides and hydrous oxides, alkali metal alkoxides such as potassium, tertiarybutoxide, tertiary amines such as triethylamine, alkali metal alkyls and aryls such as phenyllithium, and alkali metal amides such as sodium amide. Suitable solvents include any inert anhydrous solvent such as t-butanol, dimethylformamide (DMF), THF, hexamethylphosphoramide (HMPA) dioxane and the like at a temperature of from $-78°$ C. to $25°$ C., for from a few minutes to 4 hours.

(3) For the preparation of ester embodiments, of the present invention, the reaction of 1b with any of the above-listed acyl radicals in their acid form. This reaction may be conducted in the presence of a carbodiimide condensing agent such as dicyclohexylcarbodiimide or the like. Suitable solvents include any inert solvent such as $CHCl_3$, $CH_2Cl_2$, DMF, HMPA, acetone, dioxane and the like at a temperature of from $0°$ C. to $60°$ C. for from 15 minutes to 12 hours.

(4) For the preparation of ester embodiments of the present invention, the reaction of 1b with an acyl halide or an acid anhydride, wherein the acyl moiety is described above. Generally, when the above-described acylating reaction employs an acid halide (suitable halides are chloro, iodo, or bromo or acid anhydride) the reaction is conducted in an anhydrous organic solvent such as acetone, dioxane, methylenechloride chloroform, DMF, or the like in the presence of a suitable acceptor base such as $NaHCO_3$, MgO, triethylene, pyridine, and the like at a temperature of from $0°$ C. to $40°$ C. for from 1 to 4 hours.

Suitable acyl halides and anhydrides include: acetic anhydride, bromoacetic anhydride, propionic anhydride, benzoylchloride, phenylacetyl, chloride azidoacetyl chloride, 2-thienylacetyl chloride, 2-, 3- and 4-nicotinyl chloride, p-nitrobenzoyl chloride, 2,6-dimethoxybenzoyl chloride, 4-guanidinophenylacetyl chloride, hydrochloride, methanesulfonyl chloride, dibenzylphosphorochloridate, dimethylthiophosphorochloridate, 2-furoyl, ethyl carbonic anhydride, methylchloroformate, bis(p-nitrobenzyl)phosphorochloridate and the like.

(5) For the preparation of ester embodiments of the present invention, the reaction of 1b with a suitably substituted ketene or isocyanate such as ketene, dimethyl ketene, methylisocyanate, methylisothiocyanate, chlorosulfonyl isocyanate and the like. Suitable solvents include dioxane, tetrahydrofuran, chloroform and the like at a temperature of from $-70°$ C. to $60°$ C. for from 15 minutes to 18 hours.

The intermediate 2 is then N-deblocked as described above to provide starting material Ic. From Ic, Ia is prepared by deblocking the carboxyl group:

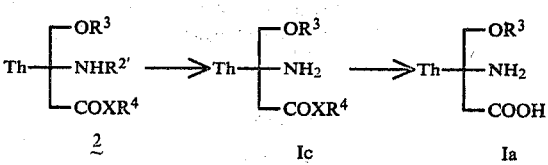

Starting material Ia is conveniently and preferably obtained when X is oxygen and $R^4$ is a readily removable carboxyl protecting or blocking group (see above). Starting material Ia is prepared by deblocking according to any of a variety of well-known procedures which include hydrolysis and hydrogenation. When the preferred carboxyl-blocking groups are employed (below), the preferred deblocking procedure is hydrogenation, wherein the intermediate species (Ic or 2) in a solvent such as a lower alkanoyl, is hydrogenated in the presence of a hydrogenation catalyst such as palladium, platinum or oxides thereof.

In this connection, it is noted that suitable "blocking groups" $R^4$ include the sub-generic groups defined above as aralkyl, haloalkyl, alkanoyloxyalkyl, alkoxyalkyl, alkenyl, substituted alkyl, or aralkoxyalkyl, and also including alkylsilyl, wherein alkyl has 1–10 carbon atoms. For example, suitable "blocking groups" $R^4$ include benzyl, phenacyl, p-nitrobenzyl, methoxymethyl, trichloroethyl, trimethylsilyl, tributyltin, p-methoxybenzyl, benzhydryl. These blocking groups are preferred since they are generally recognized easily-removable blocking groups in cephalosporin and penicillin art.

The preferred carboxyl blocking groups, are benzyl and substituted benzyl:

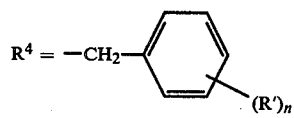

wherein n is 0–2 (n=0, R'=H) and R' is loweralkoxyl or nitro.

Preparation

The preparation of the compounds of the present invention I is conveniently described according to the definition of $R^6$. There are three cases:

(1) Amidines ($R^6$=H, or R);
(2) Guanidines ($R^6$=$NR^1R^2$); and
(3) Substituted Pseudoureas ($R^6$=OR, or SR); wherein all symbolism is as defined above.

(1) Amidines In general the compounds of Class (1) may conveniently be prepared by reacting the desired N-alkyl thienamycin (III) with an imido ester (a) or a substituted imido halide (b):

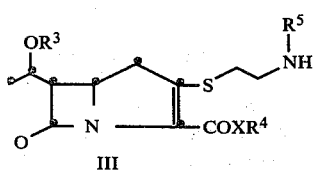

-continued

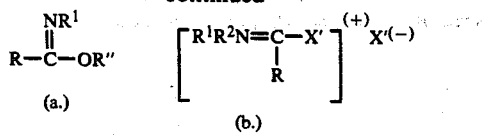

wherein $R^1$, $R^2$, and R are as defined above; $X'$ is halo such as chloro; and $-OR''$ is a leaving group wherein $R''$ is loweralkyl such as methyl, ethyl and the like.

Suitable solvents for the preparation of the compounds of Class 1 according to the above reaction schemes, depending upon the identity of the thienamycin substrate and reagent, include water, dioxane, tetrahydrofuran (THF), dimethylformamide (DMF), chloroform, acetone, acetonitrile or mixtures thereof. The reaction is conducted at a temperature of from 0° to about 25° C. for from 1 to about 6 hours. There is no criticality as to the precise identity of the reaction solvent nor the variables of reaction within the limits described above, provided only that the reaction solvent is inert or substantially inert to the intended course of reaction. Suitable reagents representatively include:

(a.) Imido Esters:

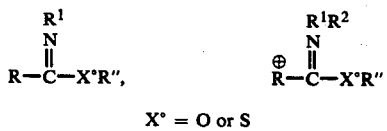

$X° = O$ or $S$

Methyl formimidate, ethyl formimidate, methyl acetimidate, ethyl acetimidate, methyl benzimidate, ethyl 4-pyridyl carboximidate, methyl phenylacetimidate, methyl 3-thienylcarboximidate, methyl azidoacetimidate, methyl chloroacetimidate, methyl cyclohexylcarboximidate, methyl 2-furylcarboximidate, methyl p-nitrobenzimidate, methyl 2,4-dimethoxybenzimidate, ethyl N=methyl formimidate, methyl N-methyl formimidate, methyl N-isopropyl formimidate, and the like.

Such imido ester reagents (a) are conveniently prepared by any of a variety of known procedures, such as:

(1) The reaction of a nitrile, RCN, with a lower alkanol in the presence of HCl according to the well-known Pinner synthesis.
(2) The reaction of a nitrile, RCN, with a lower alkanol in the presence of a base. Typically, the reaction is conducted at 0°-40° C. in the presence of an excess of the alcohol with a catalytic amount of an alkali metal alkoxide for from 15 minutes to 4 hours.
(3) The reaction of an amide,

with an alkylchloroformate, such as methylchloroformate at 25° C.-45° C. for 1-4 hours.
(4) The reaction of an N-substituted amide,

with an equivalent of an alkylating agent such as triethyloxonium fluoroborate in an inert solvent such as ether, chloroform or the like at 0°-23° C. for from 10 minutes to 2 hours.
(5) The conversion of a readily available imido ester,

($R'$ may be hydrogen), to a desired imido ester,

by reaction of the first-mentioned with an alkylamine, $R'NH_2$, in a mixture of water and an immiscible solvent such as ether or chloroform at 0°-23° C. for from 5 minutes to 1 hour.
(b) Substituted Imido Halides:

Chloropiperidino methylium chloride, chlorodimethylforminium chloride, chlorodiethyl forminium chloride, and the like.

Such imido halide reagents (b) are conveniently prepared by any of a variety of known procedures, such as:
(1) The reaction of an N,N-disubstituted amide,

with a halogenating agent such as thionyl chloride, phosgene, phosphorous pentachloride or the like in an inert solvent such as chloroform, methylene chloride and the like at 0°-40° C. for from 1-5 hours.

The reaction involving the reagents (a), may be representatively shown by the following diagram:

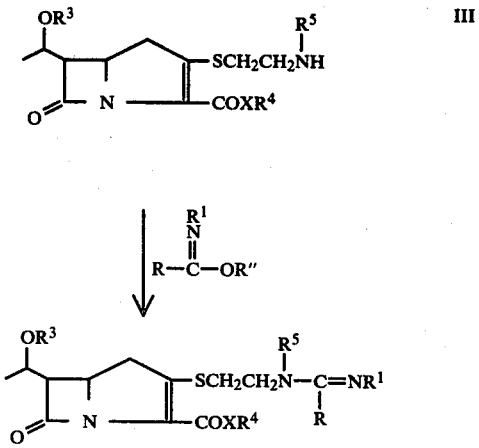

wherein $OR''$ is the leaving group of the imido ester reagent and R, $R^1$, $R^3$, $R^4$ and X are as defined above. This reaction is particularly suitable for embodiments wherein $R^3$ and $R^4$ are hydrogen and X is oxygen.

The reaction involving the reagents, (b), may representatively be shown by the following diagram:

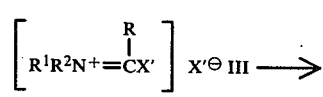

-continued

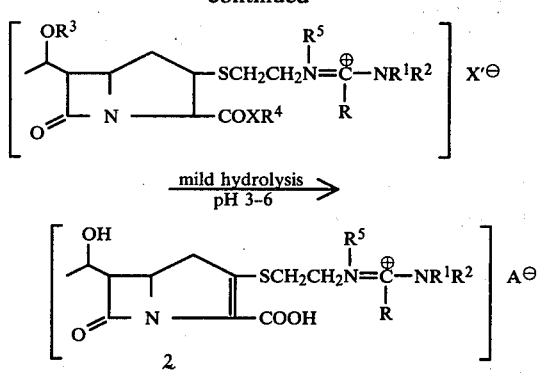

wherein all symbolism is as previously defined. When product 2 is desired, suitable values for $R^3$ and $R^4$ are trimethylsilyl and X is oxygen.

(2) Guanidines:

In general, the compounds of Class 2 may conveniently be prepared by reacting III with: (a) "an" —OR" (e.g., O-alkyl, O-aryl) pseudourea or an S-alkyl or S-aryl pseudothiourea; or (b) by reacting a compound of Class 3 (above) with ammonia or an amino compound such as an alkyl, aralkyl or heteroaralkyl amine.

Suitable solvents for such reactions include water and buffered aqueous polar organic solvent mixtures at pH 7–9 or anhydrous polar organic solvents such as dimethylformamide or hexamethylphosphoramide at a temperature of from 0° C. to 40° C. for from 1 to 24 hours.

Suitable reagents, (a) and (b), include:

(a) —OR pseudoureas and —SR pseudothioureas:

O-Methyl pseudourea, S-Methylpseudotniourea, S-methylpseudothionitrourea, O-2,4-dichlorophenyl pseudourea, S-p-nitrophenyl pseuuothiourea, O-N,N-trimethylpseudourea, and the like.

(b) Amino reagents:

Methylamine, ethylamine, 2-aminopyrimidine, dimethylamine, methyl benzylamine, 3-aminomethyl pyridine, 2-aminomethyl thiophene, ethanolamine, dimethylaminoethylamine, N-2-(aminoethyl)pyrrolidine, cyclohexylamine, n-heptylamine, isopropylamine, 2-methylallylamine, 3-phenyl-1-propylamine, 2-amino-4-picoline, 2-amino pyridine, 3-amino-4-carbethoxypyrazole, 2-aminothiazole, 5-amino-3-methyl isothiazole, and 3-amino-1,2,4-thiazole.

The reaction involving the reagents, (a), may representatively be shown by the following diagram:

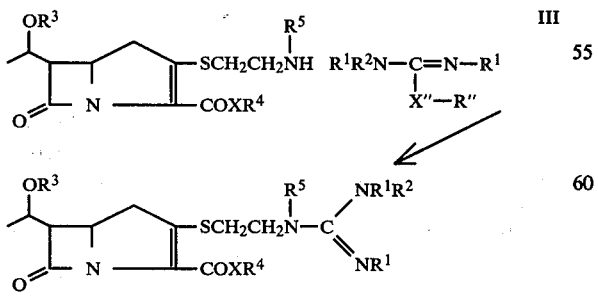

wherein $R^3$, X, $R^4$, $R^1$ and $R^2$ are as defined above; X" is O or S and R" is as defined and preferably is lower alkyl or aryl.

The reaction involving the reagents, (b), may representatively be shown by the following diagram:

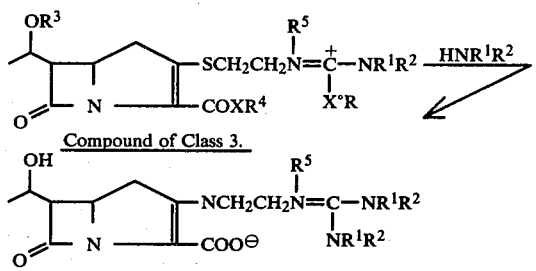

wherein $X^O$ is O or S and all other symbolism is as previously defined.

(3.) Substituted Pseudoureas:

In general, the compounds of Class 3. may conveniently be prepared by reacting a carbamyl or thiocarbamyl N-substituted Thienamycin species IVa, (see above) for example:

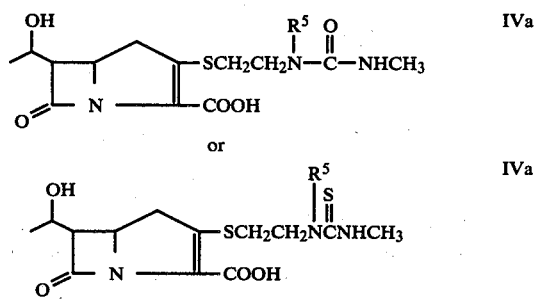

with an alkylating agent (b.) such as an active alkyl or aralkyl halide or sulfate ester.

Suitable solvents for the above reaction include lower alkanols, dioxane and acetonitrile at a temperature of from 20° C. to 60° C. for from 1 to 4 hours.

Suitable reagents IVa for above reaction scheme include N-alkyl, N-acyl thienamycins:

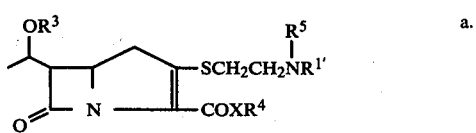

wherein $R^3$, $R^5$, X and $R^4$ are as defined above and $R^{1'}$ is acyl as defined above and preferably is selected from the group consisting of:

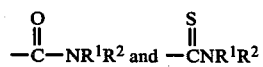

($R^1$ and $R^2$ are as defined above), such as: carbamyl, methylcarbamyl, ethylcarbamyl, phenylcarbamyl, p-bromophenylcarbamyl, phenylthiocarbamyl, methylthiocarbamyl, dimethylcarbamyl, and the like.

Suitable reagents (b.), alkylating agents, include: methyl iodide, benzyl bromide, dimethylsulfate, diethylsulfate, allyl bromide, 2-thienyl bromide, methallyl bromide, p-nitrobenzyl bromide, methyl chloromethyl ether, and the like.

The reaction involving the above reagents IVa and (b.) may representatively be shown by the following diagram:

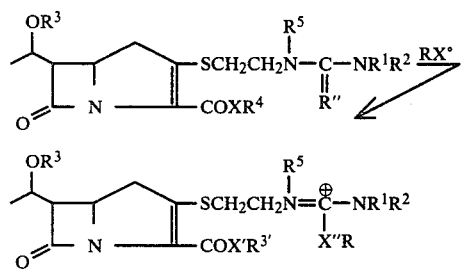

wherein X" is O or S; $X^O$ is halogen such as bromo, iodo or alkyl sulphate; $RX^O$ is the alkylating agent; and $R^1$, $R^5$, $R^2$, $R^3$, X, $R^4$ and R are as previously defined.

The products of this invention (I) form a wide variety of pharmacologically acceptable salts such as acid addition salts, e.g., with hydrochloric, hydrobromic, sulfuric, nitric, toluene-p-sulphonic and methane sulphonic acids. The salts of this invention are pharmacologically acceptable non-toxic derivatives which can be used as the active ingredient in suitable unit-dosage pharmaceutical forms. Also, they may be combined with other drugs to provide compositions having a broad spectrum of activity.

The novel compounds are valuable antibiotics active against various gram-positive and gram-negative bacteria and, accordingly, find utility in human and veterinary medicine. The compounds of this invention can therefore be used as antibacterial drugs for treating infections caused by gram-positive or gram-negative bacteria, for example, against *Staphylococcus aureus, Escherichia coli, Klebsiella pneumoniae, Serratia, Salmonella typhosa, Pseudomonas* and *Bacterium proteus*. The antibacterials of the invention may further be utilized as additives to animal feeding stuffs, for preserving foodstuffs and as disinfectants. For example, they may be employed in aqueous compositions in concentrations ranging from 0.1 to 100 parts of antibiotic per million parts of solution in order to destroy and inhibit the growth of harmful bacteria on medial and dental equipment and as bactericides in industrial applications, for example, in waterbased paints and in the white water of paper mills to inhibit the growth of harmful bacteria.

The products of this invention may be used alone or in combination as an active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, maizestarch, calcium phosphate, sorbitol or glycine, lubricants, for example, magnesium stearate, talc, polyethylene glycol, silica; disintegrants for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g. cocoa butter or other glyceride.

Compositions for injection may be presented in unit dose form in ampules, or in multidose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for reconstitution with a suitable vehicle, e.g. sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 2 to about 600 mg. of active ingredient per kg. of body weight of the subject in one or more applications per day. A preferred daily dosage for adult humans lies in the range of from about 15 to 150 mg. of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10–60%. The composition will generally contain from about 15 mg. to about 1500 mg. of the active ingredient; however, in general, it is preferable to employ a dosage amount in the range of from about 100 mg. to 1000 mg. In parenteral administration the unit dosage is usually the pure compound in a slightly acidified sterile water solution or in the form of a soluble powder intended for solution.

The following examples, illustrate but do not limit the product, process, compositional or method of treatment aspects of the present invention.

EXAMPLE 1

Preparation of N-Methyl-N-Formimidoyl thienamycin

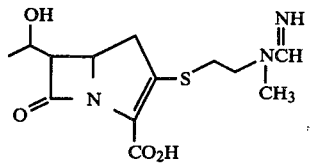

N-methyl thienamycin (14 mg) is dissolved in pH 7 0.1 N phosphate buffer (2.5 ml) and the solution adjusted to pH 8.5 using an automatic burette dispensing 1 N NaOH. While maintaining a pH of 8.5, methyl formimidate hydrochloride (25 mg) is added to the magnetically stirred solution. After 20 min. additional methyl formimidate (25 mg) is added. The reaction is allowed to proceed another 25 min and the pH is adjusted to 7.0 with 3.5 NHCl. The entire solution is then chromatographed on Dowex 50-X4 resin (26 cc, Na+ cycle, 200–400 mesh) eluted with water. The N-methyl-N-formimidoyl derivative elutes in 3-4 column volumes and is lyophilized to a white solid (3 mg).

UV (pH 7 0.1 N phosphate buffer) $\lambda_{max}$ 298 nm
IR (Nujol mull) 1760, 1710 cm$^{-1}$
NMR (100 MHz, D$_2$O) $\delta$1.32 (d, J=6 Hz, C$\underline{H}_3$—CH) 3.12 (s, NCH$_3$), 7.86

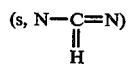

EXAMPLE 2

N-Formimidoyl-N-ethyl thienamycin

A solution of N-ethyl thienamycin (5.6 mg) in 2.8 ml of 0.2 N pH 7 phosphate buffer is adjusted to pH 8.5 and ethyl formimidate hydrochloride (50 mg) is added. The pH is maintained at 8.5 by the addition of N sodium hydroxide solution under the control of a pH stat. The mixture is stirred at 23° for 25 minutes and another portion (50 mg) of formimidate is added. After 25 minutes the reaction mixture is neutralized with dilute hydrochloric acid and chromatographed on 1.5×15 cm column of Dowex 50-X4 resin (Na+ cycle, 200–400 mesh). The column is eluted with water at a flow rate of 0.5 cc/min and the effluent is monitored by HPLC ($\frac{1}{4}''\times1'C^{18}$ Porasil; solvent 0.01 N NaHPO$_4$ solution, flow rate—2 cc/min; N-ethyl thienamycin retention time=5 min, N-formimidoyl, N-ethyl thienamycin RT=9.5 min) The combined product fractions (UV 42 ODU at $\lambda_{max}$ 298 mu) are evaporated to 5 ml and freeze dried to a white powder.

EXAMPLE 3

Silylation of N-methyl Thienamycin

To a suspension of N-methyl thienamycin (8 mg) in 1 ml of tetrahydrofuran under a stream of nitrogen is added hexamethyldisilazane (0.1 ml) and trimethylchlorosilane (20 μl). The mixture is vigorously stirred at 25° for 20 minutes then centrifuged to remove ammonium chloride. The supernatant is evaporated to an oil under a stream of nitrogen and the residual oil is used directly in further reactions.

EXAMPLE 4

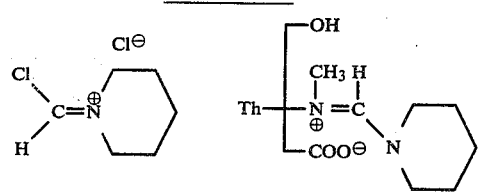

N-Methyl-thienamycin ⟶

Preparation of Thienamycin N-Methyl-N-piperidin-1-yl Methylene Derivative

N-Methyl-thienamycin (57 mg) is silylated according to the procedure previously described. The silylated antibiotic, is dissolved in methylene chloride (6 cc) in a septum stoppered flask under positive nitrogen pressure and cooled in a dry ice-acetone bath. To the magnetically stirred solution is added a solution (180 μl) of triethylamine (644 μmol) in methylene chloride. This is followed by the addition of a solution of chloropiperidinomethylium chloride (67 mg., 405 μmol) in methylene chloride (465 μl). After 1 hour in a dry ice bath, the reaction solution is rapidly added to a tetrahydrofuran—pH 7.0. 1 N phosphate buffer (1:1) solution (50 ml). The mixture is then concentrated under vacuum to 10 ml to give a homogeneous solution. The solution is washed twice with ethyl acetate (2×5 ml) and ether (2×5 ml) and briefly pumped under vacuum. This aqueous solution is then chromatographed on an XAD-2 resin column (60 ml bed). The product is eluted in 10% aqueous tetrahydrofuran (following water elution) to give the product which is recovered by lyophilization.

EXAMPLE 5

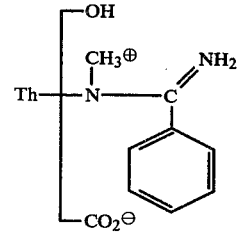

Preparation of N-Methyl-N-benzimidoyl Thienamycin

N-Methyl-thienamycin (59 mg.) is dissolved in a 33% N,N-dimethylformamide pH 7 phosphate buffer (0.05 N) solution (4.5 ml.) and adjusted to pH 9.5 using 2.5 N NaOH with an automatic dispensing burette. The solution is magnetically stirred at 25° C. and methylbenzimidate.HCl (340 mg) is added at once. After 30 min. the solution is extracted twice with an equal volume of chloroform and adjusted with dilute aqueous phosphoric acid to pH 7.0. The buffered solution is chromatographed on XAD-2 resin (65 ml.). The column is first eluted with water followed by 10% aqueous tetrahydrofuran which elutes the product. This fraction is concentrated to one-half volume and freeze-dried to give the product.

EXAMPLE 6

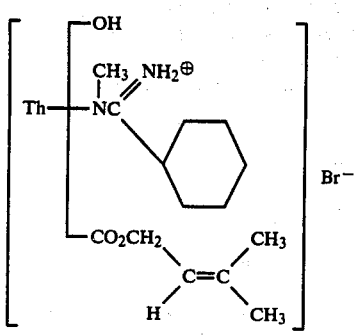

Preparation of N-Methyl N-benzimidoyl Thienomycin, 3-Methyl-2-Buten-1-yl Ester N-Methyl-N-benzimidoyl thienamycin (5.9 mg.) is dissolved in hexamethylphosphoramide (100 μl.) containing 1-bromo-3-methyl-2-butene (4.8 μl.) and triethylamine (0.5 μl.) and magnetically stirred at 22° C. After 1 hour the crude reaction is chromatographed on a 250μ thick silica gel plate developed in 8:2, chloroform, ethanol. The band of $R_f0.1-R_f0.3$ is removed and eluted with ethanol. Benzimidoyl thienamycin, 3-methyl-2-buten-1-yl ester hydrobromide is isolated as a solid after precipitation from an ethanol-chloroform solution with hexane.

EXAMPLE 7

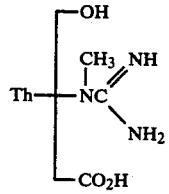

Preparation of N-Methyl-N-guanyl thienamycin

N-methyl-thienamycin (8.9 mg) is dissolved in pH 7 0.1 N phosphate buffer (0.7 ml) and N,N-dimethylformamide (0.3 ml) and the solution brought to pH 9.5 by the addition of 2.5 N sodium hydroxide solution. To the magnetically solution is added O-methylisourea.hydrogen sulfate (43 mg.) causing a slight drop in pH. Additional sodium hydroxide solution is added to bring the pH back to 9.5 and the solution is stirred 30 minutes at 23° C. The solution is then neutralized to pH 7.0. The solution containing a mixture of N-methyl thienamycin and N-methyl-N-guanyl thienamycin is chromatographed on a 20 cc of Dowex 50X4 resin (Na+ cycle, 200–400 mesh) and the product recovered by lyophilization.

EXAMPLE 8

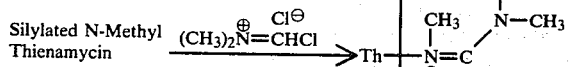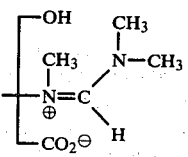

Preparation of N-Methyl-N-Dimethylaminomethylene Thienamycin

N-Methyl-thienamycin (16.5 mg) is silylated with hexamethyldisilazane (200 μl) and trimethylchlorosilane (60 μl) in the usual manner. The silylated N-methyl thienamycin is suspended in (ethanol free) chloroform (1 ml.) with magnetic stirring under a nitrogen atmosphere. The mixture is cooled to −45° C. and a solution of triethylamine (21 μl) in chloroform (21 μl) is added followed by a solution of (chloromethylene)-dimethylammonium chloride (11.5 mg) in chloroform (50 μl). The mixture is warmed to −25° C. during 1 hour and 0.1 N pH 7 phosphate buffer (5 ml) is added. The mixture is vigorously stirred 15 minutes. The aqueous phase is separated and contains N-dimethylaminomethylene thienamycin which is recovered after chromatography on Dowex 50X4 resin.

EXAMPLE 9

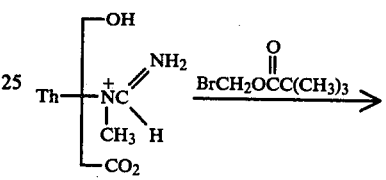

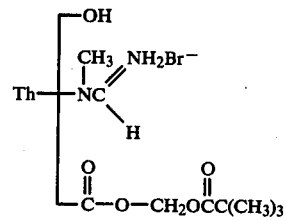

Preparation of N-Formimidoyl-N-Methyl-Thienamycin Pivaloxymethyl Ester Hydrobromide N-Formimidoyl-N-methyl thienamycin (10 mg.) is dissolved in hexamethylphosphoramide (200 μl.) containing bromomethyl pivalate (10 μl.) and triethylamine (1 μl.) and magnetically stirred at 22° C. After 2 hours the hexamethylphosphoramide solution is dissolved in 2 ml. methylene chloride and the product precipitated with a 50% hexane-ether solution. The precipitate is dissolved in an aqueous 10% tetrahydrofuran solution and chromatographed on an XAD-2 resin packed column. N-Formimidoyl-N-Methyl thienamycin pivaloxymethyl ester is isolated as a solid after tetrahydrofuran elution of the column and lyophilization.

EXAMPLE 10

Preparation of N-Ethyl-N-trifluoroacetimidoyl Thienamycin

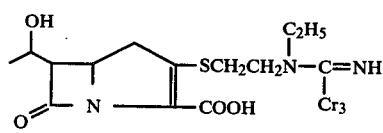

N-ethyl-thienamycin (199 mg) is dissolved in pH 7 0.1 N phosphate buffer (7 ml) and adjusted to pH 8.5 with 1 N sodium hydroxide solution. While maintaining this pH with an automatic burette, a solution of methyl trifluoroacetimidate (355 μl) in dioxane (2.5 ml) is added at once. After 30 minutes the pH is readjusted to 7.0 by the addition of 1 N hydrochloric acid. The solution is then chromatographed on Dowex 50×4 resin (200 cc, Na+ cycle, 200–400 mesh) and is eluted with water. The N-ethyl-N-trifluoroacetimidoyl thienamycin derivative elutes in the first half column volume. This eluate is rechromatographed in a similar manner on Dowex 50×4 (100 cc, Na+ cycle, 200–400 mesh) and the first column volume concentrated and chromatographed on XAD-2 resin (30 cc). The N-ethyl-N-trifluoroacetimidoyl thienamycin derivative elutes in 2.5–5.0 column volumes which is lyophilized to a white solid.

EXAMPLE 11

Preparation of N-Allyl-N-Acetimidoyl Thienamycin

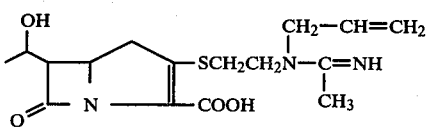

N-Allyl-thienamycin (190 mg) is dissolved in pH 7 0.1 N phosphate buffer (13 ml) and cooled in an ice bath with magnetic stirring. The solution is adjusted to pH 8.5 using 2.5 N sodium hydroxide solution dispersed from an automatic burette. While maintaining a pH of 8.5, ethyl acetimidate hydrochloride (400 mg) is added portionwise over a few minutes. After an additional 40 minutes the solution is adjusted to pH 7.0 with 2.5 N hydrochloric acid. The solution is then chromatographed on Dowex 50-X8 resin (250 cc, Na+ cycle, 100–200 mesh) and is eluted with water. The N-allyl-N-acetimidoyl derivative elutes in 1–2 column volumes (240–520 cc) and is lyophilized to a white solid.

EXAMPLE 12

Preparation of N-ethyl-N-[(4-pyridyl) (imino)methyl]thienamycin

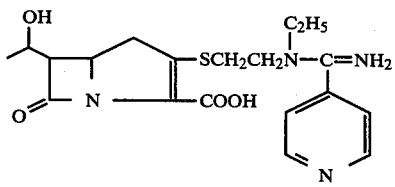

N-Ethyl-thienamycin (80 mg) is dissolved in aqueous sodium bicarbonate (24.7 mg., 0.294 mmole in 2.0 ml) at 25° C. Methyl isonicotinimidate (80 mg., 0.588 mmole) is dissolved in the solution and progress of the reaction is followed by timed aliquots using high performance liquid chromatography (HPLC): Waters instrument; 0.2×61 cm. $C_{18}$ Bondapak reverse phase column; 1.5 ml/min aqueous 10% THF; UV (254 nm) and R.I. monitors. The reaction is essentially complete in 40 minutes, and the reaction solution is chromatographed directly over an 18.4×270 mm XAD resin column, first eluting with deionised, distilled water, then changing to aqueous 10% THF. The eluate is monitored by UV and HPLC is used to locate the pure product. Correct fractions are combined and lyophilized to yield the product as a colorless, fluffy powder.

EXAMPLE 13

Following the procedure of Example 12, but replacing the reagent with an equivalent amount of methyl 4-thiazolecarboximidate, there is obtained: N-ethyl-N-[(4-thiazolyl) (imino)methyl]thienamycin.

EXAMPLE 14

Preparation of N-Allylformamide

A mixture of allylamine (5.00 g., 87.6 mmole) and methylformate (5.26 g., 87.6 mmole) is stirred at 25° C., for 2 hours. At the end of this time, the reaction flask is fitted with a short path distillation head and the desired N-allylformamide is collected at 89°–90° C./0.7 mm as a colorless oil. Yield 7.0 g. (94%). IR($CHCl_3$) 3380, 1680 $cm^{-1}$; nmr ($CHCl_3$) δ8.1 (1H, br s), δ6.4–7.9 (1H, very br), δ5.5–6.3 (1H, m), δ4.9–5.5 (2H,m), δ3.85 (2H, m).

EXAMPLE 15

Preparation of Ethyl-N-Allylformimidate Hydrochloride

Ethyl chloroformate (2.66 g., 24.47 mmole) is added by syringe to N-allylformamide (2.08 g., 24.47 mmole) in a dry flask under $N_2$. The resulting mixture is then stirred at 25° C., for 2 hours during which time $CO_2$ is rapidly evolved. The reaction mixture is then heated to 45° C. until no further evolution of gas is evident (2 hours). The viscous product is then cooled and held at a vacuum of 0.2 mm for 2 hours to remove all volatiles.

EXAMPLE 16

Preparation of Methyl N-Dimethylaminoformimidate

To a stirred solution of N,N-dimethylformhydrazide (0.22 g) in 2.0 ml of chloroform, under nitrogen, is added methylchloroformate (0.5 ml). The mixture is heated at 40° C. for three hours then evaporated under nitrogen. The mixture is triturated with anhydrous ether. The supernatant solution is decanted and the residue dried in a stream of nitrogen.

Yield: 284 mg. nmr $CDCl_3$δ, 9.13(CH); 3.80($OCH_3$), 3.01($N(CH_3)_2$).

EXAMPLE 17

Preparation of Cyclopropyl Formamide

A mixture of cyclopropylamine (5.00 g, 87.6 mmole) and methylformate (5.26 g, 87.6 mmole) is stirred at 25° C., for 2 hours. (an initial exotherm is noted). The mixture is then placed on the rotary evaporator to remove the MeOH formed in the reaction. The remaining material is distilled through a short path head to yield 6.92 g (93%) of the desired N-cyclopropyl formamide as a colorless oil, n.m.r. ($CDCl_3$) δ8.1 (1H, br S), 6.8–8.5 (1H, br), δ2.4–3.0 (1H, m), δ0.4–1.0 (4H,m).

EXAMPLE 18

Preparation of Ethyl N-Cyclopropyl Formimidate

Ethylchloroformate (4.078 g, 37.58 mmole) is added by syringe to N-cyclopropylformamide (3.194 g, 37.58 mmole) in a dry flask under $N_2$. After an induction period of 30 sec., a rapid evolution of gas begins. The resulting reaction mixture is stirred at 25° C. until no further evolution of gas can be detected (~4 hr), then the viscous product is subjected to a vacuum of 0.5 mm for 1 hr to remove any unreacted ethyl chloroformate. NMR analysis of the product shows the formyl proton at 9.37 as a broad singlet. ($CDCl_3$ solution).

EXAMPLE 19

Preparation of N-Ethyl-N'-Dimethylamino-N-Formimidoyl Thienamycin

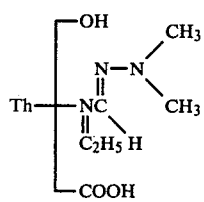

N-Ethyl Thienamycin (115 mg) is dissolved in pH 7 0.1 N phosphate buffer (7 ml) and the pH of the solution is adjusted to 8.5 using an automatic burette dispensing 1 N NaOH. To this stirred solution is added methyl N-dimethylaminoformimidate hydrochloride (284 mg) while the pH is maintained at 8.5. After 20 minutes the pH of the solution is adjusted to 7.0 using 2.5 N HCl and the solution is chromatographed on Dowex 50-X4 resin (53 cc, Na+ cycle, 200–400 mesh) eluted with deionized water. The chromtography is carried out in a water jacketed column at 3°. The N-Ethyl N'-dimethylamino-N-formimidoyl derivative elutes in 2 column volumes and is lyophilized to a white solid.

EXAMPLE 20

Preparation of N,N'-Dimethyl-N-Formimidoyl Thienamycin

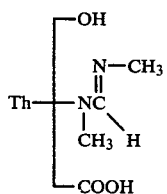

N-Methyl thienamycin (140 mg) is dissolved in pH 7 0.1 N phosphate buffer (10 ml) and the pH of the solution is adjusted to 8.5 using an automatic burette dispensing 1 N NaOH. To this solution is added methyl N-methyl formimidate hydrochloride (200 μl) while the pH is maintained at 8.5. After 40 minutes the pH is adjusted to 7.0 using 2.5 N HCl and the solution is chromatographed on Dowex 50-X4 resin (72 cc, Na+ cycle, 200–400 mesh) eluted with deionized water. The N,N'-dimethyl-N-formimidoyl derivative elutes in 2 column volumes and is lyophilized to a white solid.

EXAMPLE 21

Preparation of N,allyl, N'-Benzyl-N-Formimidoyl Thienamycin

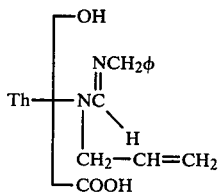

N-Allyl-thienamycin (110 mg.) is dissolved in pH 7 0.1 N phosphate buffer (7 ml.) and the pH of the solution is adjusted to 8.5 using an automatic burette dispensing 1 N NaOH. A solution of ethyl N-benzyl formimidate fluoroborate (572 mg) in p-dioxane (2 ml) is added to the buffered solution while the pH is maintained at 8.5. After 20 minutes the pH of the solution is adjusted to 7.0 using 2.5 N HCl and chromatographed on Dowex 50-X4 resin (53 cc, Na+ cycle, 200–400 mesh) eluted with deionized water. The chromatography is carried out in a water jacketed column at 3°. The N-allyl-N'-benzyl-N-formimidoyl derivative elutes in 2 column volumes and is lyophilized to a white solid.

EXAMPLE 22

Preparation of N-ethyl-N'-isopropyl-N-formimidoyl thienamycin

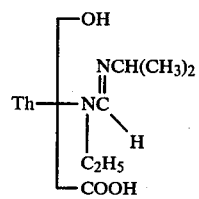

N-ethyl-thienamycin (110 mg) is dissolved in pH 7 0.1 N phosphate buffer (7 ml.) and the Ph of the solution is adjusted to 8.5 using an automatic burette dispensing 1 N NaOH. A solution of methyl N-isopropyl formimidate hydrochloride (300 mg.) in p-dioxane (1 ml.) is added to the magnetically stirred buffered solution while the pH is maintained at 8.5. After 25 minutes the pH of the solution is adjusted to 7.0 using 2.5 N NaOH and chromatographed on Dowex 50-X4 resin (53 cc, Na+ cycle, 200–400 mesh) eluted with deionized water. The chromatography is carried out in a water jacketed column at 3° C. The N-ethyl-N'-isopropyl-N-formimidoyl derivative elutes in 2 column volumes and is lyophilized to a white solid.

EXAMPLE 23

Preparation of N-Methyl-N(N'-Allyl-Formimidoyl)Thienamycin

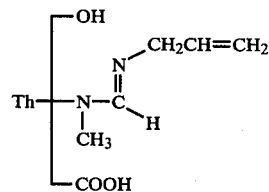

To a prechilled sample of thienamycin (123 mg., 0.452 mmols) is added 13 ml. of cold 0.1 N phosphate buffer. The solution is adjusted to pH 9 with N sodium hydrochloride. To this basic solution at 2° C. is added all at once ethyl N-allyl-formimidate hydrochloride (0.3 g). The pH drops to 7.3 and is brought back to 8.5 with additional sodium hydroxide. The reaction mixture is stirred at 2° C. for an additional 30 min. and the pH is adjusted to 7 with cold 0.1 N sulfuric acid. The reaction mixture is chromatographed on a Dowex-50 X 4 column (60 ml., 200–400 mesh) eluting with water at a flow rate of 0.5 ml/cm² of resin bed. After discarding the first 400 ml of eluate, the next 150 ml. is lyophilized to give the product.

EXAMPLE 24

Preparation of N-Methyl-N(3-azidopropionimidoyl)Thienamycin

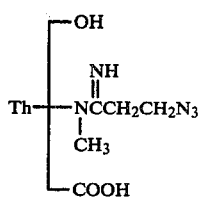

To a solution of N-methyl-thienamycin (133 mg) in 10 ml. 0.1 M pH 7.0 phosphate buffer is added 1.2 g of O-ethyl-3-azidopropionimidate.HCl while the solution is maintained at pH 8.5 with 2.5 N NaOH. The mixture is stirred at 0° C. for 0.5 hr., then is neutralized with 2.5 N HCl to pH 7.0, concentrated to 5 ml. and chromatographed on a Dowex 50W X 8 (Na form) column (1.5"×12") which is eluted with water to give the desired product.

EXAMPLE 25

Preparation of N-Methyl-N(3-aminopropionimidoyl)thienamycin

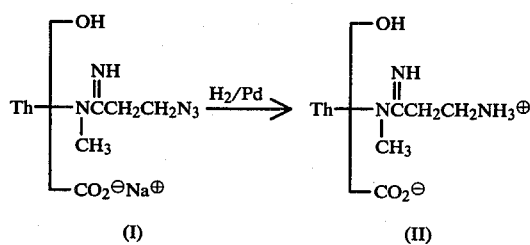

EXAMPLE 26

Preparation of N-Methyl-N-Nitroguanyl Thienamycin

N-Methyl-thienamycin (131 mg) is dissolved in a solution of dimethyl sulfoxide (10 ml), tri-n-butylamine (0.30 ml), and 2-methyl-1-nitro-2-thiopseudourea (0.3 g). The solution is heated in a water bath at 45° C. while a stream of nitrogen is vigorously bubbled into the solution. After 50 min. the solution is concentrated under high vacuum to 1.0 ml. and dissolved in 0.05 N pH 7 phosphate buffer (7 ml). The unreacted thiopseudourea is precipitated and removed by filtration. The solution is then chromatographed on Dowex 50-X4 resin (53 cm³, 200–400 mesh, Na+ cycle) and eluted with water. The N-nitroguanyl dericaive elutes in the first column volume and is lyophilized to a solid.

EXAMPLE 27

Preparation of Ethyl N-Benzylformimidate

A solution of 690 mg (5.1 mmoles) of N-benzylformamide in 5 ml of methylene chloride is cooled in an ice-water bath and put under an argon blanket. The solution is stirred while 4.9 ml (4.9 mmoles) of 1 M triethyloxonium fluoroborate in methylene chloride is added dropwise. After a 45 minute reaction time, the mixture is concentrated to dryness under reduced pressure at room temperature, and the residue is dried under reduced pressure over $P_2O_5$. The nuclear magnetic resonance spectrum of the product in deuterochloroform is fully in accord with the product being a fluoroborate etherate complex of ethyl N-benzylformimidate.

EXAMPLE 28

Preparation of N-isopropyl formamide

Formamide (1.13 g, 0.98 ml) is dissolved in 10 ml of toluene, containing toluenesulfonic acid (4.7 g). To the above mixture is added isopropylamine (2.95 g., 4.25 ml). The mixture is refluxed overnight under a gentle stream of $N_2$. The solution is filtered and the toluene is evaporated under reduced pressure. The residual oil is distilled at 59°–62° C./0.07 mn to give 1.0 g of the desired product.

EXAMPLE 29

Preparation of Methyl N-isopropyl formimidate

Isopropyl formamide (535 mg) is treated with an equivalent amount of ethyl chloroformate (440 μl) for 2—2 hours under $N_2$ at 40°–45° C. The mixture is washed successively with petroleum ether anhydrous ether and benzene leaving the product as an oil.

EXAMPLE 30

Preparation of N-ethyl-N-[N'-cyclopropylformimidoyl]thienamycin

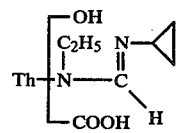

N-Ethyl-thienamycin (100 mg) in 10 ml 0.1 M, pH 7.0 phosphate buffer is adjusted and maintained at pH 8.5–9.0 while 300 mg of ethyl N-cyclopropylformimidate hydrochloride is added dropwise to the solution. The mixture is stirred at 23° for 40 minutes, then is neutralized, and chromatographed on a Dowex-50 X 8 (Na form) ion-exchange column (1.5"×10"). The column is eluted with water, collecting 6.5 ml fractions. Fractions 43–95 are combined, concentrated and freeze-dried to give the solid product.

EXAMPLE 31

Preparation of O,N-Dimethyl-N-(p-Nitrobenzyloxycarbonyl)-Thienamycin-p-Nitrobenzyl Ester

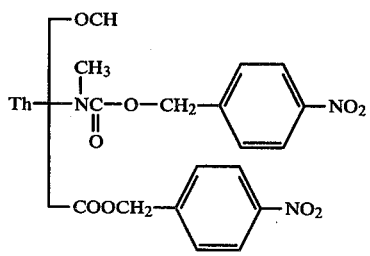

Step A

N-Methyl-N-(p-Nitrobenzyloxycarbonyl)thienamycin Lithium Salt

To N-methyl thienamycin (220 mg. in 60 ml. water at 0° C.) is added successively, 679 NaHCO₃, 60 ml dioxane and then with stirring 1.1 equivalents p-nitrobenzylchloroformate over a period of 1.5 minutes. The mixture is allowed to react 10 minutes, and is then extracted three times with cold ethyl ether. Electrophoresis (0.05 M, pH 7, phosphate buffer, 50 V/cm., 20 minutes) shows no free N-methyl thienamycin present. The aq. extract is adjusted to pH 2.2 with 1 M $H_3PO_4$ solution and extracted three times with EtOAc. The EtOAc extract is dried over $MgSO_4$, filtered and reextracted 0.1 N LiOH, to pH 8.2. The final pH is adjusted to 7.0 with 1 M $H_3PO_4$ and the sample lyophilized.

Step B

N-Methyl-N-(p-Nitrobenzyloxycarbonyl)-Thienamycin(p-nitrobenzyl)ester

A mixture of p-nitrobenzyloxycarbonyl-N-methyl-thienamycin lithium salt (295 mg) and 0.4 g of p-nitrobenzyl bromide in 3 ml of hexamethyl phosphoramide is stirred for 3 hours at 25° C. The solution is diluted with 50 ml of ethyl acetate and extracted successively with water (3 portions), pH 7 phosphate buffer and saturated sodium chloride solution. The organic phase is dried over magnesium sulfate and evaporated to 5 ml causing the product to crystallize. The crystals are collected and washed with ethyl acetate.

Step C

O,N-Dimethyl-N-(p-Nitrobenzyloxycarbonyl)-thienamycin(p-Nitrobenzyl Ester

To a solution of 135 mg. of N-methyl-N-p-nitrobenzyloxycarbonyl thienamycin-(p-nitrobenzyl) ester in 50 ml. of methylene chloride at 0° C. is added with vigorous stirring 0.5 ml of 0.006 M fluoboric acid in ether-methylene chloride (3:1) immediately followed by 10 ml of a cooled solution of 0.6 M diazomethane in methyle chloride. The diazomethane is decolorized in one minute. The solution is extracted with 10 ml of 0.1 N phosphate buffer, dried and evaporated to a small volume. The solution is applied to two 8"×8" 1000μ silica gel plates which are developed with 3:1 ethylacetate-chloroform. The band containing O,N-dimethyl N-p-nitrobenzyloxycarbonyl thienamycin p-nitrobenzylester is eluted with ethylacetate and the product is recovered by evaporation of the eluate.

EXAMPLE 32

O,N-Dimethyl Thienamycin

A solution of 20 mg. of O,N-Dimethyl N-(p-nitrobenzyloxycarbonyl)thienamycin-p-nitrobenzyl ester in 2 ml of tetrahydrofuran and 1 ml of ethanol is hydrogenated at 50 psig, 23° C. in the presence of 20 mg of platinum oxide for 2½ hours. The catalyst is filtered and 1 ml of 0.1 N pH 7 phosphate buffer is added to the filtrate. The solution is evaporated under reduced pressure to 2 ml and the mixture is taken up in 5 ml of water and 5 ml of ethylacetate and centrifuged. The ethylacetate layer is removed and the aqueous layer is extracted again with ethylacetate and with ether and then filtered through Celite. The aqueous solution is applied to a column (20 ml) of XAD-2 resin. The column is first eluted with water and then with 10% tetrahydrofuran. The tetrahydrofuran eluate is concentrated and lyophilized giving substantially pure O,N-dimethyl thienamycin.

EXAMPLE 33

Preparation of O,N-Dimethyl-N-Formimidoyl Thienamycin

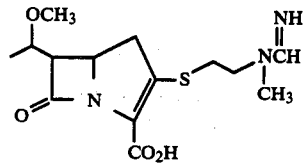

O,N-Dimethyl thienamycin (14 mg) is dissolved in pH 7.0 1 N phosphate buffer (2.5 ml) and the solution adjusted to pH 8.5 using an automatic burette dispensing 1 N NaOH. While maintaining a pH of 8.5, methyl formimidate hydrochloride (25 mg) is added to the magnetically stirred solution. After 20 min. additional methyl formimidate (25 mg) is added. The reaction is allowed to proceed another 25 min and the pH is adjusted to 7.0 with 2.5 N HCl. The entire solution is then chromatographed on Dowex 50-X4 resin (26 cc, Na+ cycle, 200–400 mesh) eluted with water. The O,N-Dimethyl-N-formimidoyl derivative eluates in 3–4 column volumes and is recovered by lyophilization.

EXAMPLE 34

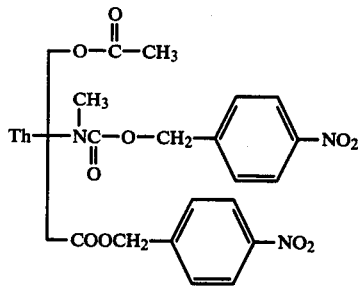

Preparation of O-Acetyl-N-Methyl-N-(p-nitrobenzyloxycarbonyl)-thienamycin-(p-nitrobenzyl)ester To a solution of 50 mg of N-methyl-N-(p-nitrobenzyloxycarbonyl thienamycin)-p-nitrobenzylester in 0.5 ml of pyridine is added 0.16 ml of acetic anhydride. The mixture is allowed to react at 25° C., for three hours, then pumped to dryness under vacuum. The solid residue is dissolved in chloroform and chromatographed on an 8"×8" 1000μ silica gel plate in 3:1 ethylacetate-chloroform yielding o-acetyl-N-methyl-N-p-nitrobenzyloxycarbonyl thienamycin p-nitrobenzyl ester.

EXAMPLE 35

O-Acetyl-N-methyl thienamycin

A solution of 20 mg. of O-acetyl-N-methyl-N-(p-nitrobenzyloxycarbonyl)thienamycin-p-nitrobenzyl ester in 2 ml of tetrahydrofuran and 1 ml of ethanol is hydrogenated at 50 psig, 23° C. in the presence of 20 mg of platinum oxide for 2½ hours. The catalyst is filtered and 1 ml of 0.1 N pH 7 phosphate buffer is added to the filtrate. The solution is evaporated under reduced pressure to 2 ml and the mixture is taken up in 5 ml of water and 5 ml of ethylacetate and centrifuged. The ethylacetate layer is removed and the aqueous layer is extracted again with ethylacetate and with ether and then filtered through Celite. The aqueous solution is applied to a column (20 ml) of XAD-2 resin. The column is first eluted with water and then with 10% tetrahydrofuran. The tetrahydrofuran eluate is concentrated and lyophilized giving substantially pure O-acetyl-N-methyl thienamycin.

EXAMPLE 36

Preparation of O-Acetyl-N-Methyl-N-Formimidoyl thienamycin

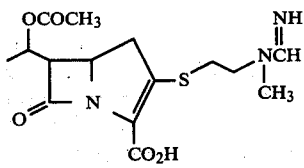

O-Acetyl-N-methyl thienamycin (14 mg) is dissolved in pH 7 0.1 N phosphate buffer (2.5 ml) and the solution adjusted to pH 8.5 using an automatic burette dispensing 1 N NaOH. While maintaining a pH of 8.5, methyl formimidate hydrochloride (25 mg) is added to the magnetically stirred solution. After 20 min. additional methyl formimidate (25 mg) is added. The reaction is allowed to proceed another 25 min and the pH is adjusted to 7.0 with 2.5 N HCl. The entire solution is then chromatographed on Dowex 50-X4 resin (26 cc, Na+ cycle, 200-400 mesh) eluted with water. The fractions containing O-acetyl-N-methyl-N-formimidoyl thienamycin are combined and lyophilized.

EXAMPLE 37

Following the procedure set forth in the foregoing text and examples, the following compounds of the present invention are obtained. The reagents, imido ethers and imido halides, utilized in the reaction with thienamycin, or a derivative thereof, to provide the following compounds are either known, or may be prepared as described above.

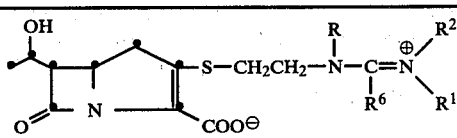

| Compound | R | $R^6$ | $R^1$ | $R^2$ |
|---|---|---|---|---|
| 1. | $CH_3$ | $CH_3$ | H | H |
| 2. | $CH_3$ | $CH_3$ | $CH_3$ | $CH_3$ |
| 3. | $CH_3$ | $CH_3$ | $CH_3$ | H |
| 4. | $CH_3$ | $N(CH_3)_2$ | H | H |
| 5. | $CH_3$ | $CR_3$ | H | H |
| 6. | $CH_3$ | 4-pyridyl | H | H |
| 7. | $CH_3$ | 2-pyridyl | H | H |
| 8. | $CH_3$ | 3-pyridyl | H | H |
| 9. | $CH_3$ | thiazolyl | H | H |
| 10. | $CH_3$ | H | $-CH_2CH_2-S-CH_3$ | H |
| 11. | $CH_3$ | H | $-CH(CH_2)_3$ | H |
| 12. | $CH_3$ | H | $-CH(CH_3)_3$ | H |
| 13. | $CH_3$ | H | $-CH_2CH_3$ | H |
| 14. | $CH_3$ | H | $-CH_2-CH=CH_2$ | H |
| 15. | $CH_3$ | H | $-CH_2-C=CH_2$ <br> $\quad\quad\;\;\|$ <br> $\quad\quad\;\;CH$ | H |
| 16. | $CH_3$ | H | cyclopropyl | H |
| 17. | $CH_3$ | $CH_2CH_3$ | H | H |
| 18. | $CH_3$ | H | $-CH_2CF_3$ | H |
| 19. | $CH_3$ | H | $-CH_2COOM$ | H |
| 20. | $CH_3$ | H | $-OCH_3$ | H |
| 21. | $CH_3$ | H | $CH_2CH=CH-CH_3$ | H |
| 22. | $CH_3$ | H | $-CH_2-$cyclopropyl | H |
| 23. | $CH_3$ | H | cyclobutyl | H |

4,309,438

-continued

| | | | | |
|---|---|---|---|---|
| 24. | CH$_3$ | H | cyclopentyl | H |
| 25. | CH$_3$ | H | cyclohexyl | H |
| 26. | CH$_3$ | H | phenyl | H |
| 27. | CH$_3$ | H | cyclopentyl | H |
| 28. | CH$_3$ | H | —CH$_2$—phenyl | H |
| 29. | CH$_3$ | H | —phenyl-OCH$_3$ | H |
| 30. | CH$_3$ | H | —phenyl-NH$_2$ | H |
| 31. | CH$_3$ | H | —phenyl(CH$_3$) | H |
| 32. | CH$_3$ | H | —phenyl(Cl) | H |
| 33. | CH$_3$ | H | —CH$_2$CH$_2$N(morpholino) | H |
| 34. | CH$_3$ | H | —CH$_2$CH$_2$—phenyl | H |
| 35. | CH$_3$ | H | —CH$_2$—phenyl—OH | H |
| 36. | CH$_3$ | H | —CH$_2$—phenyl—S—CH$_3$ | H |
| 37. | CH$_3$ | H | —CH$_2$—phenyl—N(CH$_3$)$_2$ | H |
| 38. | CH$_3$ | H | CH$_3$ | C$_2$H$_5$ |
| 39. | CH$_3$ | H | C$_2$H$_5$ | C$_2$H$_5$ |
| 40. | CH$_3$ | H | CH$_3$ | CH(CH$_3$)$_2$ |
| 41. | CH$_3$ | H | CH$_3$ | φ |
| 42. | CH$_3$ | H | CH$_3$ | CH$_2$CH=CH$_2$ |
| 43. | CH$_3$ | —C=CH$_2$ | H | H |
| 44. | CH$_3$ | thienyl-OCH$_3$ | H | H |
| 45. | CH$_3$ | furyl | H | H |
| 46. | CH$_3$ | N-methylpyrrolyl | H | H |
| 47. | CH$_3$ | triazinyl-CH$_3$ | H | H |
| 48. | CH$_3$ | imidazolyl (NH) | H | H |
| 49. | CH$_3$ | H | —CH$_2$-thiazolinyl | H |
| 50. | CH$_3$ | N-methylimidazolyl | H | H |

-continued

| | R | R' | R" | |
|---|---|---|---|---|
| 51. | CH₃ | CH₃ | —C₂H₅ | H |
| 52. | CH₃ | CH₃ | —CH(CH₃)₂ | H |
| 53. | CH₃ | CH₃ | —CH₃ | —C₂H₅ |
| 54. | CH₃ | CH₃ | —C(CH₃)₃ | H |
| 55. | CH₃ | H | —CH—C≡CH | H |
| 56. | —C₂H₅ | CH₃ | H | H |
| 57. | —C₂H₅ | H | —CH₃ | H |
| 58. | —C₂H₅ | H | —CH₃ | CH₃ |
| 59. | —C₂H₅ | CH₃ | —CH₃ | H |
| 60. | —CH₂φ | H | H | H |
| 61. | —CH₂φ | H | —CH₃ | H |
| 62. | —CH₃ | H | —CH₂CH₂OH | H |
| 63. | CH₃ | H | —CH₂CH₂N(CH₃)₂ | H |
| 64. | CH₃ | H | —CH₂CH₂N(CH₃)₂ | H |
| 65. | CH₃ | NH₂ | CH₃ | H |
| 66. | CH₃ | NH₂ | CH₃ | CH₃ |
| 67. | CH₃ | NH—CH₃ | H | H |
| 68. | CH₃ | NHCH₃ | CH₃ | H |
| 69. | CH₃ | NH₂ | NH₂ | H |
| 70. | CH₃ | SCH₃ | H | H |
| 71. | CH₃ | SCH₃ | CH₃ | H |
| 72. | CH₃ | H | OCH₃ | H |
| 73. | CH₃ | —CH₂Br | H | H |
| 74. | CH₃ | —CH₂N(CH₃)₂ | H | H |

| Compound | R | R' | R" | X | Y | A⊖ |
|---|---|---|---|---|---|---|
| 75. | CH₃ | —CH₂CH=C(CH₃)₂ | H | NH₂ | H | Cl |
| 76. | CH₃ | —CH₂—⌬—OCH₃ | H | NH₂ | H | Cl |
| 77. | CH₃ | —CH₂OC(=O)—C(CH₃)₃ | H | NHCH₃ | H | Cl |
| 78. | CH₃ | —CH₂OCC(CH₃)₃ (=O) | H | NH₂ | CH₃ | CH₃COO |
| 79. | C₂H₅ | —CH₂O—C(=O)—C(CH₃)₃ | H | NH₂ | H | Cl |
| 80. | CH₃ | —CH₂CH₂—S—CH₃ | H | NH₂ | CH₃ | H₂PO₄ |
| 81. | CH₃ | —CH₂—O—C(=O)—CH₃ | H | NHCH₃ | H | Cl |
| 82. | CH₃ | —CH₂—C(=O)—φ | H | NH₂ | H | Cl |
| 83. | CH₃ | -5-indanyl | H | NH₂ | H | Cl |
| 84. | CH₃ | phthalidyl | H | NH₂ | H | Cl |
| 85. | CH₃ | Na | SO₃⊖ | NH₂ | H | — |
| 86. | CH₃ | Na | PO₃H⊖ | NH₂ | H | — |
| 87. | CH₃ | —CH₂OC(=O)—C(CH₃)₃ | SO₃— | NH₂ | H | — |
| 88. | CH₃ | —CH₂—O—C(=O)—C(CH₃)₃ | PO₃H⊖ | NH₂ | H | — |

EXAMPLE 38

Preparation of Pharmaceutical Compositions

One such unit dosage form consists in mixing 120 mg. of N-Methyl,N-Formimidoyl thienamycin with 20 mg. of lactose and 5 mg. of magnesium stearate and placing the 145 mg. mixture into a No. 3 gelatin capsule. Similarly, by employing more of the active ingredient and less lactose, other dosage forms can be put up in No. 3 gelatin capsules and should it be necessary to mix more than 145 mg. of ingredients together, larger capsules such as compressed tablets and pills can also be prepared. The following examples are illustrative of the preparation of pharmaceutical formulations:

| TABLET | PER TABLET |
|---|---|
| N-Methyl,N-Formimidoyl thienamycin | 125 mg. |
| Cornstarch, U.S.P. | 6 mg. |
| Dicalcium Phosphate | 192 mg. |
| Lactose, U.S.P. | 190 mg. |

The active ingredient is blended with the dicalcium phosphate, lactose and about half of the cornstarch. The mixture is then granulated with 15% cornstarch paste (6 mg) and rough-screened. It is dried at 45° C. and screened again through No. 16 screens. The balance of the cornstarch and the magnesium stearate is added and the mixture is compressed into tablets, approximately 0.5 inch in diameter each weighing 800 mg.

PARENTERAL SOLUTION
Ampoule:

| Ampoule: | |
|---|---|
| N-Methyl,N-Formimidoyl thienamycin | 500 mg. |
| OPTHALMIC SOLUTION | |
| N-Methyl,N-Formimidoyl thienamycin | 100 mg. |
| Hydroxypropylmethyl | 5 mg. |
| Sterile Water to | 1 ml. |
| OTIC SOLUTION | |
| N-Methyl,N-Formimidoyl thienamycin | 100 mg. |
| Benzalkonium chloride | 0.1 mg. |
| Sterile Water to | 1 ml. |
| TOPICAL OINTMENT | |
| N-Methyl,N-Formimidoyl thienamycin | 100 mg. |
| Polyethylene Glycol 4000 U.S.P. | 400 mg. |
| Polyethylene Glycol 400 U.S.P. | 1.0 gram |

The active ingredient in the above formulations may be administered alone or in combination with other biologically active ingredients as, for example, with other antibacterial agents such as lincomycin, a penicillin, streptomycin, novobiocin, gentamicin, neomycin, colistin and kanamycin, or with other therapeutic agents such as probenecid.

What is claimed is:

1. A compound having the structure:

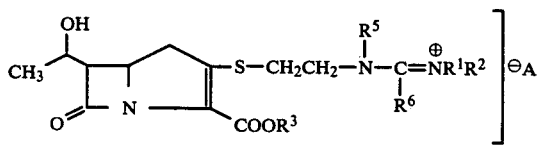

wherein A is a pharmaceutically acceptable counter ion; $R^5$ is a member selected from the group consisting of loweralkyl, loweralkenyl, and benzyl; $R^6$ is a member selected from the group consisting of hydrogen, loweralkyl, loweralkenyl, loweralkylthio, phenyl, pyridyl, thiazolyl and $-NR^1R^2$; $R^1$ and $R^2$ independently are members selected from the group consisting of hydrogen, lower alkyl, loweralkenyl, cycloloweralkyl, mono- and di-loweralkylamino, phenyl and benzyl; and $R^3$ is a member selected from the group consisting of hydrogen and pivaloxymethyl.

2. A compound according to claim 1 having the structure:

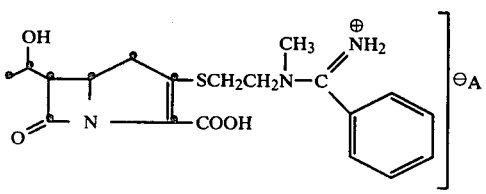

3. A compound according to claim 1 having the structure:

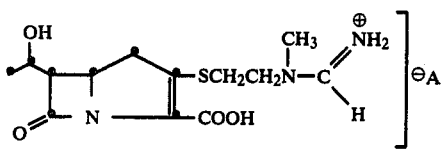

4. A compound according to claim 1 having the structure:

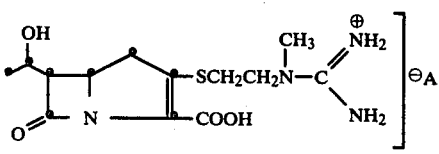

5. A compound according to claim 1 having the structure:

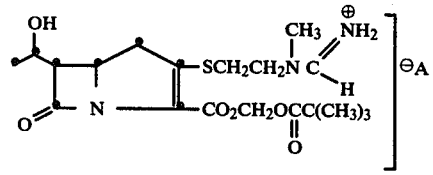

wherein A is a pharmaceutically acceptable anionic salt moiety.

6. The compound according to claim 1 having the structure:

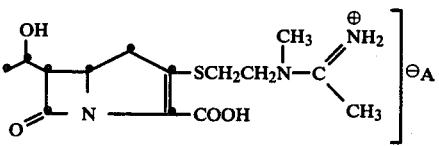

7. A compound according to claim 1 having the structure:

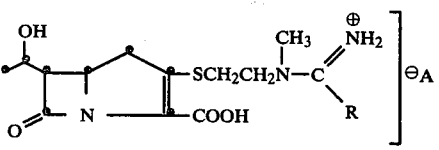

wherein R is 4-pyridyl.

8. A compound according to claim 1 having the structure:

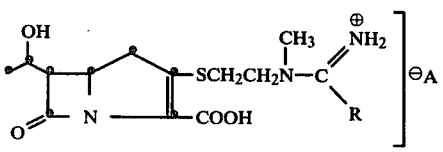

wherein R is 4-thiazolyl.

9. A compound according to claim 1 having the structure:

10. A compound according to claim 1 having the structure:

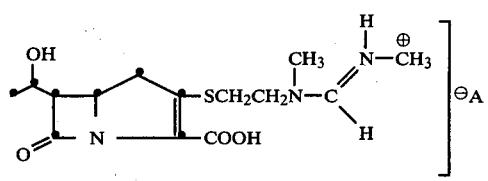

11. A compound according to claim 1 having the structure:

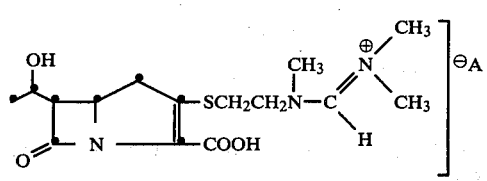

12. A compound according to claim 1 having the structure:

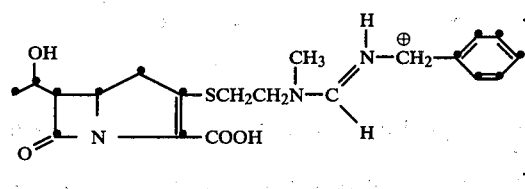

13. A compound according to claim 1 having the structure:

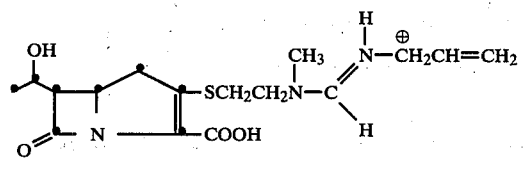

14. A compound according to claim 1 having the structure:

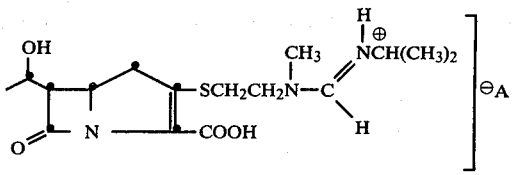

15. A compound according to claim 1 having the structure:

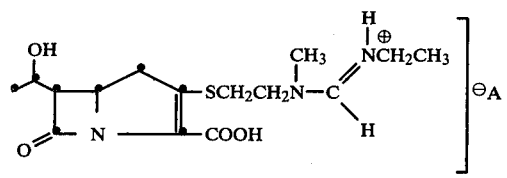

16. A compound according to claim 1 having the structure:

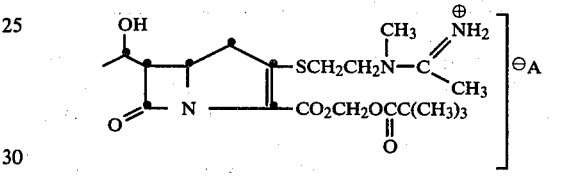

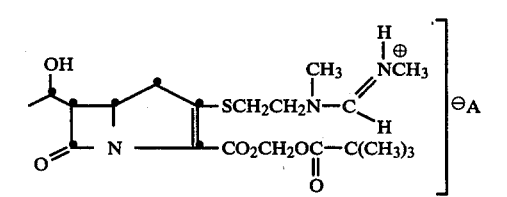

17. An antibacterial pharmaceutical composition consisting essentially of in unitary dosage form a therapeutically effective amount of a compound according to claim 1 and a pharmaceutical carrier therefor.

* * * * *